(12) United States Patent
Barnett et al.

(10) Patent No.: US 7,435,263 B2
(45) Date of Patent: Oct. 14, 2008

(54) MODULAR LONG BONE PROSTHESIS FOR PARTIAL OR TOTAL BONE REPLACEMENT

(75) Inventors: Gary D. Barnett, Wabash, IN (US); Scott C. Brown, Warsaw, IN (US); Mark B. Lester, Warsaw, ID (US)

(73) Assignee: DePuy Products, Inc., Warsaw, IN (US)

( * ) Notice: Subject to any disclaimer, the term of this patent is extended or adjusted under 35 U.S.C. 154(b) by 874 days.

(21) Appl. No.: 10/675,064

(22) Filed: Sep. 30, 2003

(65) Prior Publication Data

US 2005/0071014 A1 Mar. 31, 2005

(51) Int. Cl.
*A61F 2/40* (2006.01)
*A61F 2/32* (2006.01)

(52) U.S. Cl. ............... 623/19.12; 623/22.42; 623/23.47

(58) Field of Classification Search ............... 623/19.12, 623/19.13, 19.14, 20.11, 20.12, 20.13, 22.4, 623/22.41, 22.42, 22.45, 22.46, 23.15, 23.18, 623/23.39, 23.47
See application file for complete search history.

(56) References Cited

U.S. PATENT DOCUMENTS

| | | | |
|---|---|---|---|
| 4,384,373 A | 5/1983 | Sivash | |
| 4,404,691 A | 9/1983 | Buning et al. | |
| 4,502,160 A | 3/1985 | Moore et al. | |
| 4,676,797 A | 6/1987 | Anapliotis et al. | |
| 4,892,546 A | 1/1990 | Kotz et al. | |
| 4,908,032 A | 3/1990 | Keller | |
| 5,026,399 A | 6/1991 | Engelbrecht et al. | |
| 5,314,479 A | 5/1994 | Rockwood, Jr. et al. | |
| 5,330,531 A | 7/1994 | Capanna | |
| 5,358,524 A | 10/1994 | Richelsoph | |

(Continued)

OTHER PUBLICATIONS

Stryker Corporation, Homedica Osteonics, Corp. brochure: MRS: *Modular Replacement System: For use in adult and pediatric reconstruction*, © 1997/1999. single page.

(Continued)

*Primary Examiner*—Bruce Snow
(74) *Attorney, Agent, or Firm*—Maginot, Moore & Beck

(57) ABSTRACT

A modular long bone prosthesis is provided having a proximal component and a retroversion component. The proximal component is configured at a proximal end to receive a head forming a portion of a joint and is formed at a distal end to mate with additional prosthesis components. The proximal component is formed to simulate an angle inherent in the proximal end of the bone to be replaced and includes an indicator adjacent the distal end to facilitate rotational alignment of the proximal component and additional prosthesis components. The retroversion component includes a proximal end configured to mate with the distal end of the proximal component. The proximal end includes alignment indicia for positioning relative to the indicator on the proximal component. When the indicator is in a first position relative to the alignment indicia the proximal component and the retroversion component establish a first alignment orientation forming an angle simulating the angle inherent in the proximal end of the right long bone of the long bone to be replaced. When the indicator is in a second position relative to the alignment indicia the proximal component and the retroversion component establish a second alignment orientation forming an angle simulating the angle inherent in the proximal end of the left long bone of the long bone to be replaced.

17 Claims, 10 Drawing Sheets

U.S. PATENT DOCUMENTS

| | | | |
|---|---|---|---|
| 5,387,239 A | | 2/1995 | Bianco et al. |
| 5,645,607 A | * | 7/1997 | Hickey .................... 623/23.35 |
| 5,702,457 A | | 12/1997 | Walch et al. |
| 5,702,464 A | * | 12/1997 | Lackey et al. ............ 623/20.32 |
| 5,702,479 A | | 12/1997 | Schawalder |
| 5,776,200 A | * | 7/1998 | Johnson et al. .......... 623/20.15 |
| 6,102,956 A | | 8/2000 | Kranz |
| 6,149,687 A | * | 11/2000 | Gray et al. ............... 623/20.34 |
| 6,193,758 B1 | | 2/2001 | Huebner |
| 6,290,725 B1 | | 9/2001 | Weiss et al. |
| 6,440,171 B1 | * | 8/2002 | Doubler et al. .......... 623/22.42 |
| 6,613,092 B1 | * | 9/2003 | Kana et al. ............... 623/20.15 |
| 2004/0220673 A1 | * | 11/2004 | Pria ........................ 623/19.12 |
| 2005/0256582 A1 | * | 11/2005 | Ferree ..................... 623/17.16 |

OTHER PUBLICATIONS

Biomet, Inc. brochure: *Proximal Humeral Replacement System*, © 1996. single page.

Biomet, Inc. brochure: *Features & Benefits*, Mosaic Proximal Humeral Replacement, © 2002. single page.

\* cited by examiner

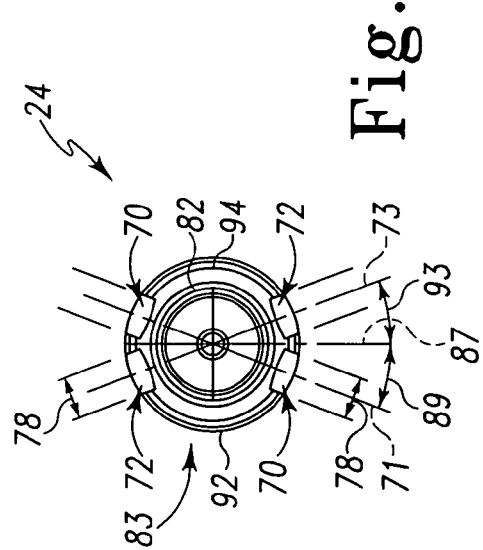
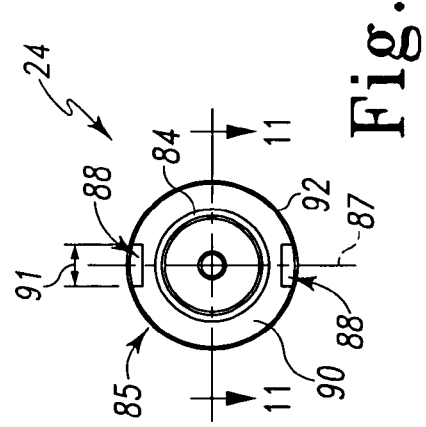
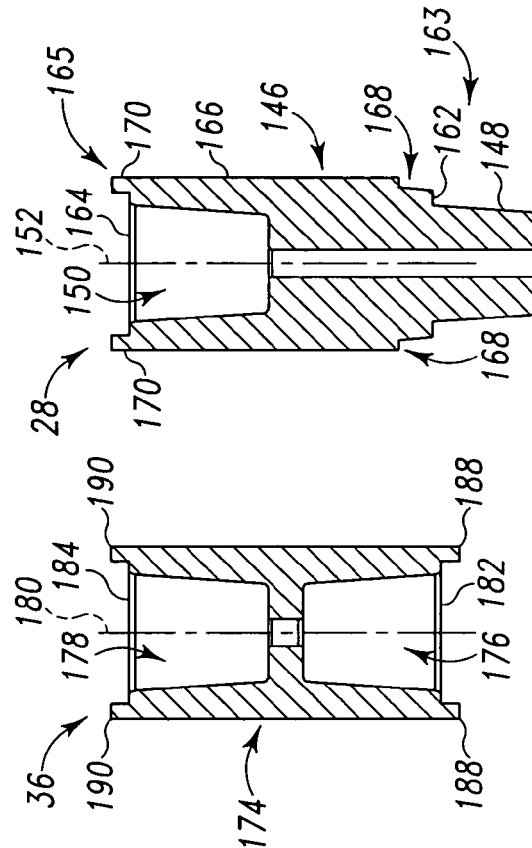
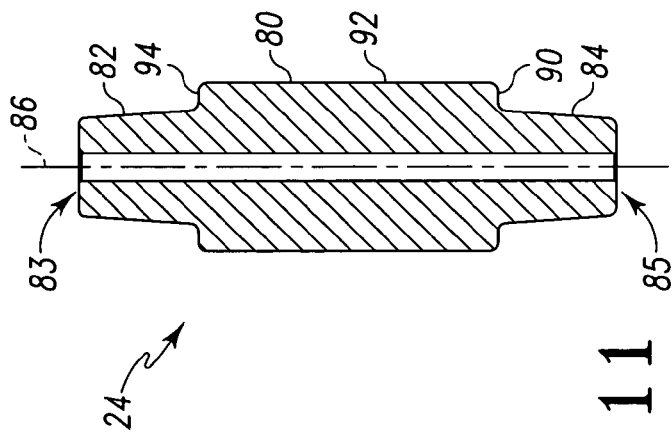
Fig. 9
Fig. 10
Fig. 11
Fig. 12
Fig. 13

MODULAR LONG BONE PROSTHESIS FOR PARTIAL OR TOTAL BONE REPLACEMENT

BACKGROUND AND SUMMARY

The present invention relates to an orthopedic prosthesis. More specifically, the invention concerns prosthesis for restoring the functionality of an extremity, such as an arm of a patient. The invention is particularly suited for the replacement of all or any part of a right or left long bone of the patient.

The later half of the 20th century has seen a proliferation in the number of human skeletal components that can be replaced by a man-made prosthesis. Over the years these prosthesis have evolved from simply a physical substitution for a bone or a joint, to the more sophisticated fully functional prosthesis. For example, prostheses are well known for the replacement of the shoulder joint or the elbow joint. A modular shoulder prosthesis designed according to U.S. Pat. No. 5,314,479, assigned to DePuy, Inc., can be integrated into the existing glenoid cavity of a patient's shoulder. The prosthesis includes a lower stem that is configured to be embedded within the existing humerus bone of the patient. In a like manner, U.S. Pat. No. 6,290,725 (also owned by Depuy, Inc.) discloses a modular elbow prosthesis that includes stems for implantation into the intramedullary canal of the humerus and ulna bones. Similar prosthetic joints exist for replacement of the hip, knee, and ankle joints.

While many devices exists for the replacement of a damaged or defective joint, the substitution of a bone, and particularly a long bone, is much more problematic. While prosthetic phalanges have enjoyed increasing success, the long bones have not been so easily replaced by prosthesis, particularly to maintain the functionality of the patient's limb.

The problems with long bone replacement are many and varied. Perhaps the greatest difficulty is the extreme load-bearing nature of the long bones. A further problem associated with a long bone prosthesis is the variability in length of a particular long bone between patients. The femur, tibia, ulna, and humerus bones vary in length as much as patients vary in height. Many approaches have been implemented for adjusting the length of prosthetic joints. It should be noted that with these prosthetic joints, the joint is affixed to an existing long bone, such as by implantation of a stem into the intramedullary canal of the bone.

Yet an additional problem with total long bone prosthesis is that it is difficult to provide a prosthesis of the appropriate length prior to surgery because it is difficult to obtain an accurate pre-surgical measurement of the long bone. Inaccurate measurement of the long bone prosthesis of course leads to an improper length of the extremity. This mal-adjusted length can cause motor and muscular difficulties. Moreover, an incorrect prosthesis length can affect the tightness of the tissue surrounding the prosthesis. If the length is too short, the surrounding tissue is unnecessarily loose. If the prosthesis is too long, the tissue may be too tight, if the prosthesis can be implanted at all. Thus when a surgeon is to replace a long bone or a part of it with a prosthesis, it is desirable to have a prosthesis available of the anticipated length based upon pre-surgical measurement which can be easily lengthened or shortened.

Maintaining sufficient prosthetic devices to address the needs of total, proximal, distal and intercalary replacement of both the right and left long bones of patients can require a large inventory of prosthetics either at the hospital or a nearby medical supply company.

While the prior prosthetic devices have gone a long way toward helping patients with bone or joint disorders, several needs remain unmet. One need is for a viable long bone prosthesis or substitute that is suitable for replacement of the right or left long bone of a patient. Another need is for an adjustable length prosthesis that allows for easy and ready adjustments by substitution of parts during the surgery to implant the prosthesis within the patient. Another need is for a prosthetic system using common components to fabricate total, proximal, distal, and intercalary long bone prosthesis for both the right and left long bone.

In order to address these needs, the present invention contemplates a modular long bone prosthesis that can be readily configured using the same components as a right or left long bone total replacement. By substitution of standard components the length of the prosthesis can be varied.

According to one aspect of the disclosure, a modular long bone prosthesis is provided having a proximal component and a retroversion component. The proximal component is configured at a proximal end to receive a head forming a portion of a joint and is formed at a distal end to mate with additional prosthesis components. The proximal component is formed to simulate an angle inherent in the proximal end of the bone to be replaced and includes an indicator adjacent the distal end to facilitate rotational alignment of the proximal component and additional prosthesis components. The retroversion component includes a proximal end configured to mate with the distal end of the proximal component. The proximal end includes alignment indicia for positioning relative to the indicator on the proximal component. When the indicator is in a first position relative to the alignment indicia the proximal component and the retroversion component establish a first alignment orientation forming an angle simulating the angle inherent in the proximal end of the right long bone of the long bone to be replaced. When the indicator is in a second position relative to the alignment indicia the proximal component and the retroversion component establish a second alignment orientation forming an angle simulating the angle inherent in the proximal end of the left long bone of the long bone to be replaced.

According to a second aspect of the disclosure, a modular long bone prosthesis system is provided for replacing all or a portion of a long bone having a head and neck at its proximal end and a pivot axis about which the bone with which the long bone articulates pivots at the distal end. The system comprises a proximal component configured to replace the neck of the long bone and to receive a component for replacing the head at a proximal end, a distal component configured at its distal end to include a pivot axis about which the bone with which the long bone articulates may pivot, a retroversion component, a spacer component, and a stem component. The proximal component is configured to mount to either the retroversion component, the stem component or the spacer component on its distal end. The distal component is configured on its proximal end to mount to either the retroversion component, the stem component or the spacer component. The retroversion component is configured to mount at one end to either the distal component or the spacer component and at the other end to either the proximal component or the spacer component. The spacer component is configured at one end to mount to either the distal component or the proximal component and at the other end to either the retroversion component or the stem component. The stem component is configured at one end to mount to either the distal component, the proximal component or the spacer component and at the other end to be received in the intramedullary canal of the long bone. When coupled, the proximal component, distal component and retroversion component form a total long bone prosthesis exhibiting a retroversion angle found in the long bone. When coupled, the proximal and stem components form a proximal prosthesis. When coupled, the distal and stem components form a distal prosthesis.

According to yet another aspect of the disclosure, a modular humeral prosthesis system is provided for replacing all or part of either a right or left human humerus having a head forming a retroversion angle with the pivot axis of the forearm. The system comprises a proximal component configured to replace the neck of the humerus and to receive a component for replacing the head of the humerus at a proximal end, a distal component configured at its distal end to include a pivot axis about which the forearm pivots, a retroversion component, a plurality of spacer components, and a stem component. The proximal component is configured on its distal end to mount to either the retroversion component, the stem component or one of the plurality of the spacer components. The distal component is configured on its proximal end to mount to either the retroversion component, the stem component or one of the plurality of the spacer component. The retroversion component is configured to mount at one end to either the distal component or one of the plurality of the spacer components and at the other end to either the proximal component or the one of the plurality of spacer components. Each spacer component is configured at one end to mount to either the distal component or the proximal component and at the other end to either the retroversion component or the stem component. One of the plurality of spacer components is longer than the other of the plurality of spacer components. The stem component is configured at one end to couple to either the distal component, the proximal component or the spacer component and configured at the other end to be received in the intramedullary canal of the long bone. The proximal component, distal component and retroversion component when coupled form a total humeral prosthesis exhibiting a retroversion angle found in the humerus. The proximal and stem components when coupled form a proximal humeral prosthesis. The distal and stem components when coupled form a distal humeral prosthesis.

Additional features and advantages of the present invention will become apparent to those skilled in the art upon consideration of the following detailed description of preferred embodiments exemplifying the best mode of carrying out the invention as presently perceived.

BRIEF DESCRIPTION OF THE FIGURES

In describing the disclosed device, reference will be made to the following figures in which:

FIG. 9 is a proximal end elevation view of the retroversion component of FIG. 1;

FIG. 10 is a distal end elevation view of the retroversion component of FIG. 1;

FIG. 11 is a sectional view of the retroversion component taken along line 11-11 of FIG. 10;

FIG. 12 is a sectional view of the spacer segment taken along line 12-12 of FIG. 1;

FIG. 13 is a sectional view of the intercalary segment taken along line 13-13 of FIG. 1;

DETAILED DESCRIPTION OF THE PREFERRED EMBODIMENTS

Figure 1:
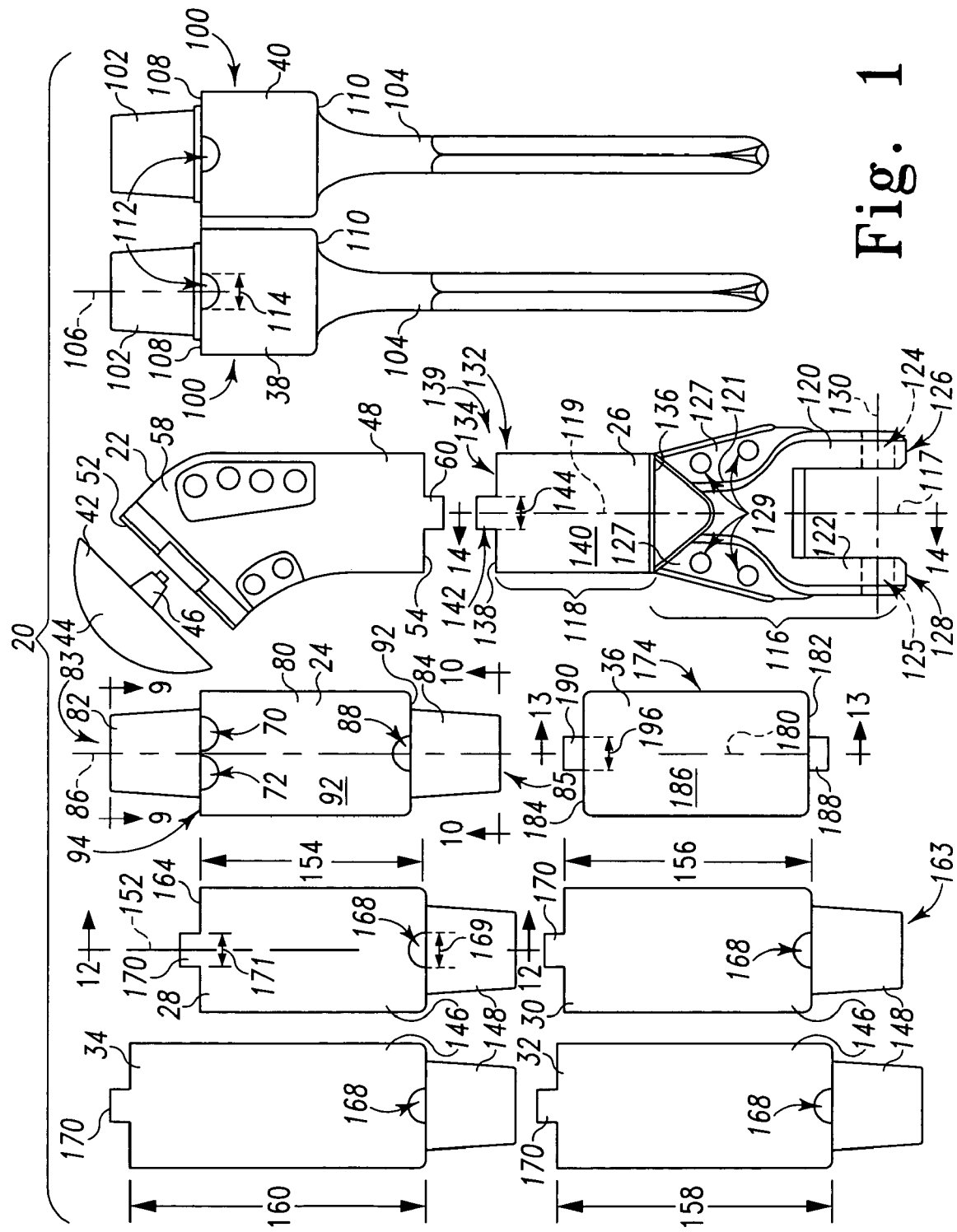
FIG. 1 is a plan view of components of the disclosed modular long bone prosthesis system for configuration to act as a total bone, proximal, distal and intercalary prosthesis showing a first embodiment of a proximal component, a first embodiment of a retroversion component, four spacer segment components, an intercalary component, a head and two stem components.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
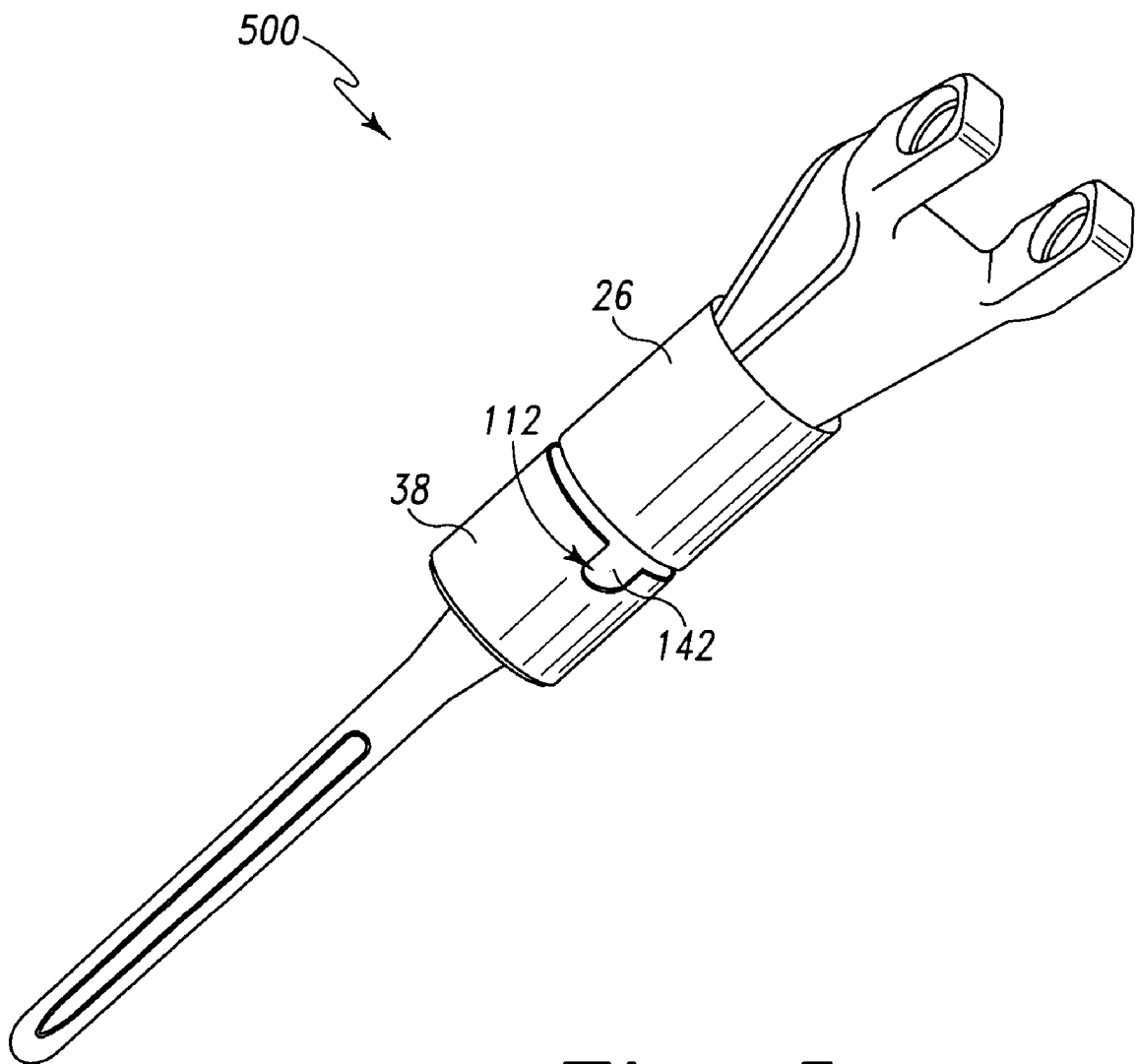
FIG. 5 is a perspective view of a modular long bone prosthesis configured for distal bone replacement having the distal component mated to the stem component of FIG. 1.
Figure 6:
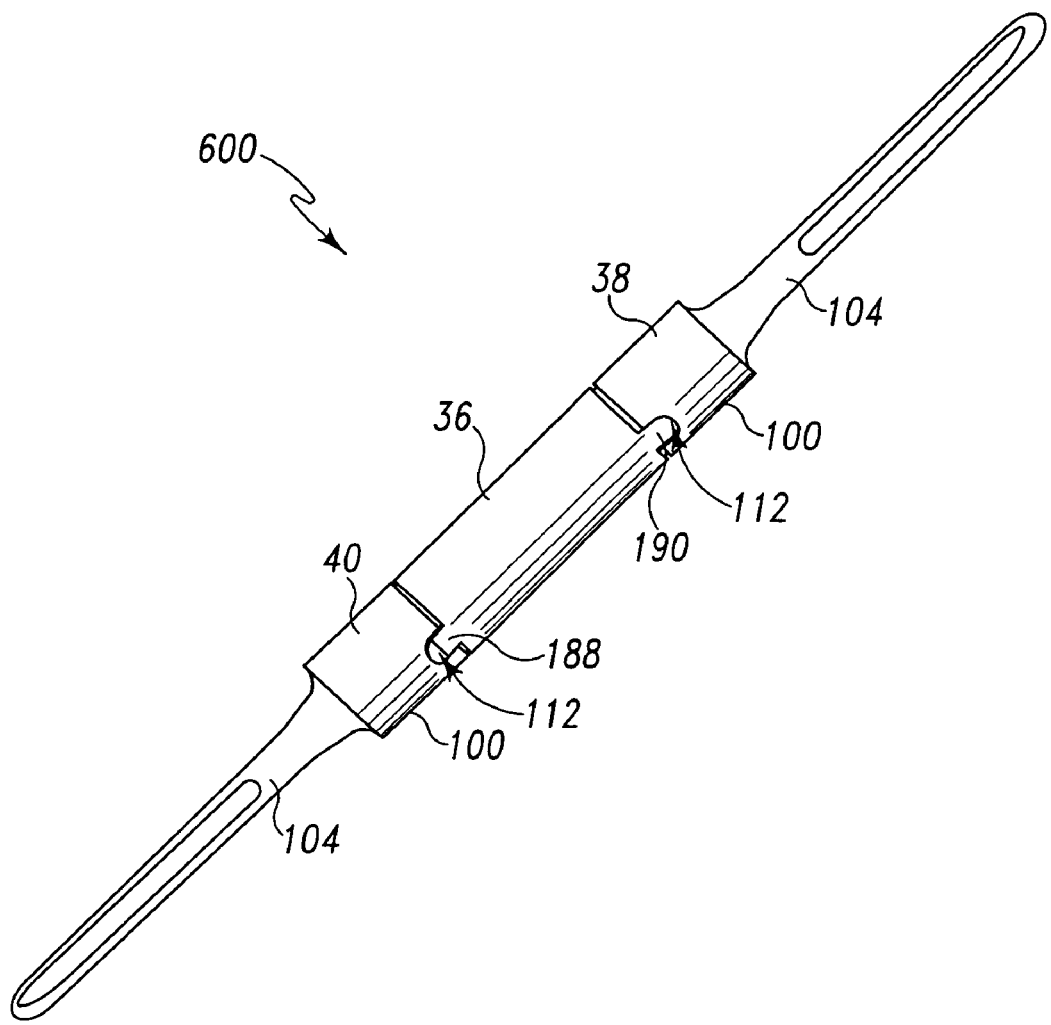
FIG. 6 is a perspective view of a modular long bone prosthesis configured for intercalary bone replacement having the two stem components mated to the long bone component of FIG. 1.

The disclosure contemplates a modular long bone prosthesis system or kit 20 that permits components to be assembled to act as a right long bone total replacement 200 (FIG. 2), a left long bone total replacement 300 (FIG. 3), a proximal long bone replacement 400 (FIG. 4), a distal long bone replacement 500 (FIG. 5) or an intercalary replacement 600 (FIG. 6). Each of the configurations of the prosthesis is adjustable in length to approximate the length of the long bone being replaced. In the total replacement configurations 200, 300 (FIGS. 2-3) the prosthesis has application for the replacement or substitution of a long bone of a patient, such as the humerus bone. However, the adjustability features of the present invention can be implemented for other prosthesis 400, 500, 600 and other prosthetic joints.

Referring now to FIG. 1, the components of the modular long bone prosthesis system or kit 20 are shown. The components of the modular prosthesis system 20 include a proximal component 22, a retroversion segment 24, a distal component 26, a first spacer segment 28, a second spacer segment 30, a third spacer segment 32, a fourth spacer segment 34, an intercalary segment 36, a first stem component 38, a second stem component 40 and a head 42. Each component is configured to mate with other components to form prosthesis. The illustrated components are specifically adapted for use as humeral prosthesis although the teachings are applicable to other long bone prosthesis such as femural prosthesis. The long bone prosthesis system 20 disclosed herein is a modular system including various components 22, 24, 26, 28, 30, 32, 34, 36, 38, 40, 42 that can be assembled to create a right total humeral prosthesis 200, a left total humeral prosthesis 300, a proximal humeral prosthesis 400, a distal humeral prosthesis 500 and/or an intercalary humeral prosthesis 600 as well as variants of the illustrated prosthesis.

The components of the illustrated kit 20 are illustrative, it being anticipated that fewer or additional components will be included in the kit. For example, head 42 is representative of a plurality of heads including centrally mounted heads and eccentrically mounted heads of various diameters, configurations and sizes. Similarly, stem component 38, 40 are a pair of identically configured stem components having identical bodies and stems representative of a plurality of stems similarly configured except for the diameter and length of the stem.

Each head 42 is of the type commonly known for use in the bone to be replaced by the prosthesis fabricated from the kit 20. Since the illustrated kit 20 is specifically adapted for fabrication of humeral prosthesis, head 42 is representative of the plurality of heads commonly provided in shoulder arthroplasty systems such as the Global™ Advantage® Shoulder Arthroplasty System available from DePuy Orthopaedics, Inc., Warsaw, Ind., a Johnson & Johnson company. Similar heads 42 are described and depicted in Rockwell, Jr. et al., U.S. Pat. No. 5,314,479 assigned to Depuy, Inc., the disclosure of which is hereby incorporated herein by this reference. Head 42 includes a curved bearing surface 44 mounted to a stem 46. Stem 46 is illustratively a tapered stem 46 of a tapered frictional locking system. In the illustrated embodiment, stem 46 is received in a socket 66 in the proximal component 22 and locked therein using a Morse taper lock. Those skilled in the art will recognize that other systems may be used for mounting head 42 to proximal portion 22 within the scope of the disclosure including other taper lock systems or other mounting systems.

Since the illustrated modular prosthesis system 20 is used to form humeral prosthesis, certain aspects of the description will reference additional prosthetic components with which the illustrated components interact. The illustrated prosthesis is adapted to mate with components of the Global™ Advantage® Shoulder Arthroplasty system and the Acclaim™ Total Elbow System both available from DePuy Orthopaedics, Inc, Warsaw, Ind., a Johnson & Johnson company.

Figure 2:
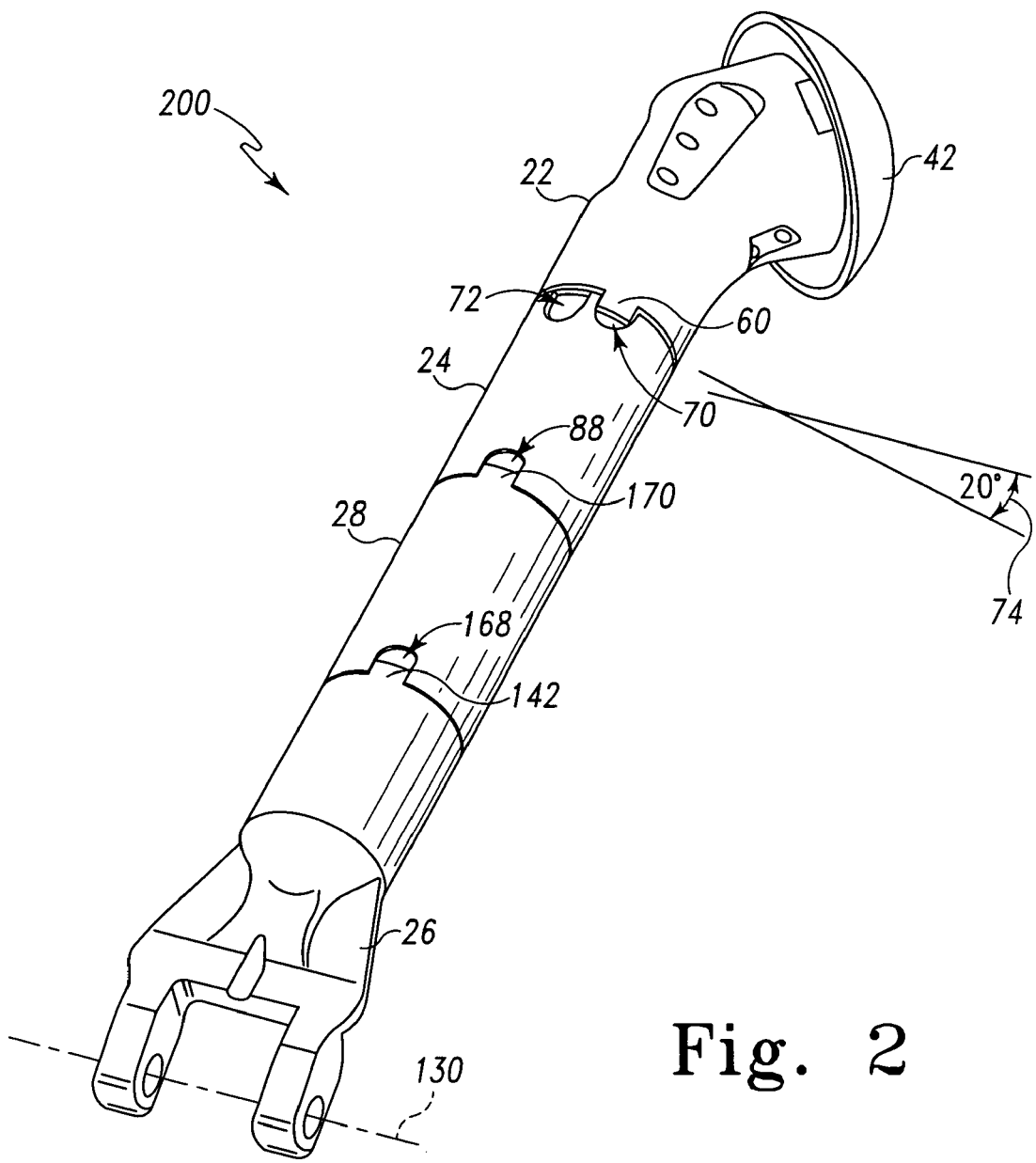
FIG. 2 is a perspective view of a modular long bone prosthesis configured for total bone replacement using the proximal component, the retroversion segment, a spacer segment, the distal component and the head of FIG. 1 to form a right long bone total prosthesis.
Figure 3:
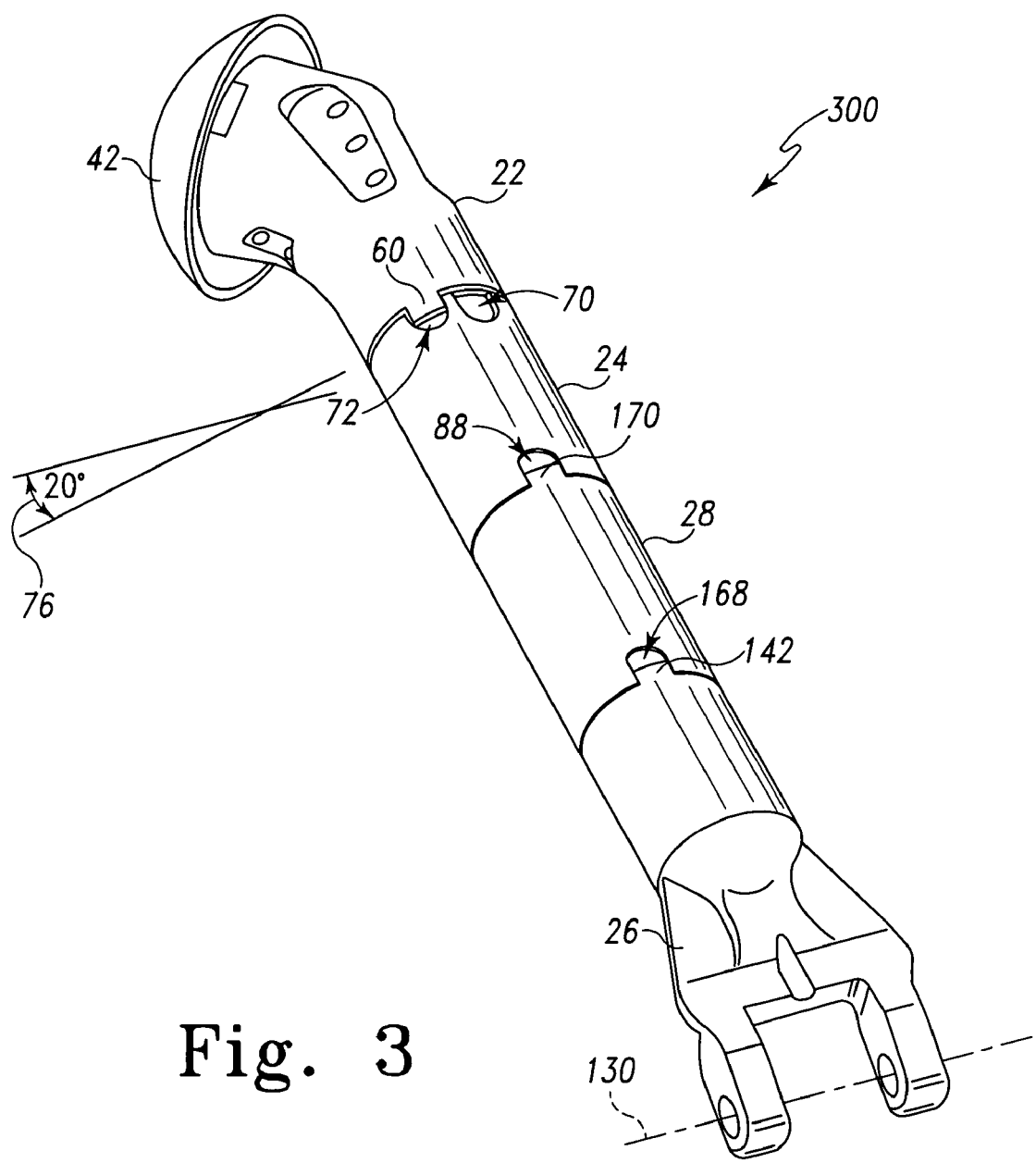
FIG. 3 is a perspective view of a modular long bone prosthesis configured for total bone replacement using the proximal component, the retroversion segment, the spacer segment, the distal component and the head of FIG. 1 to form a left long bone total prosthesis.

As shown for example, in FIGS. 2 and 3, the modular prosthesis system 20 is designed to form a right or a left total bone prosthesis by mating a head 42, a retroversion segment 24, a distal component 26, a first spacer segment 28 and a proximal component 22. The surgeon, surgical team or other personnel mate the components 22, 24, 26, 28 and 42 in a manner that permits a surgeon to form a right total bone prosthesis 200 (FIG. 2) or a left total bone prosthesis 300 (FIG. 3) having the appropriate retroversion angle for the patient's bone being replaced.

While FIGS. 2 and 3 illustrate total humeral prosthesis 200, 300 being formed using the head 42, a retroversion segment 24, a distal component 26, a first spacer segment 28 and a proximal component 22, it is within the scope of the disclosure for total humeral prosthesis to be formed using only the head 42, proximal portion 22, retroversion portion 24 and distal portion 26, when a shorter prosthesis than the illustrated total bone prosthesis 200, 300 is desired. Additionally, it is within the scope of the disclosure for a total humeral prosthesis to be formed using the head 42, proximal portion 22, retroversion portion 24 and distal portion 26 and one of the second spacer segment 30, third spacer segment 32 and fourth spacer segment 34 when a longer total bone prosthesis than the illustrated total bone prosthesis 200, 300 is desired. Those skilled in the art will recognize that a total humeral prosthesis may be formed, within the scope of the disclosure using head 42, proximal portion 22, retroversion portion 24 and distal portion 26 and one or more of the first spacer segment 28, second spacer segment 30, third spacer segment 32 and fourth spacer segment 34, alone or in combination, to obtain a prosthesis closely approximating the length of the humerus being replaced.

In use, a health care provider may select one or a combination of the spacer segments 28, 30, 32, 34 and the other components 42, 22, 24, 26 of the total humeral prosthesis prior to surgery on the basis that the selected component, when assembled, will form a total humeral prosthesis having a length approximating the pre-surgical measurement of the humerus. Additional non-selected spacer segments 28, 30, 32, 34 are made available to the surgeon during the surgery for substituting for or adding to the selected components and segments to adjust the length of the prosthesis if the pre-surgical measurement of the humerus was inaccurate.

In the total humeral prosthesis 200, 300 illustrated in FIGS. 2 and 3, a first embodiment of the proximal component 22 and a first embodiment of the retroversion segment 24 are used. In the first embodiment, a set of tabs 60 is formed on the distal end 54 of the proximal component 22 and two sets of slots 70, 72 are formed on the proximal end 83 of the retroversion segment 24. When the proximal component 22 and the retroversion segment 24 are mated and the set of tabs 60 are received in the centers of the first set of slots 70 the proximal component 22 and retroversion segment 24 are configured to provide a twenty degree retroversion angle 74 for a right humeral prosthesis 200. When the proximal component 22 and the retroversion segment 24 are mated and the set of tabs 60 are received in the centers of the second set of slots 72, the proximal component 22 and retroversion segment 24 are configured to provide a twenty degree retroversion angle 76 for a left humeral prosthesis 300.

In the illustrated embodiments, the widths 78 of each slot 70, 72 of the sets of slots is equal to or slightly greater than the widths 62 of each tab 60 of the set of tabs so that when assembled the proximal component 22 and retroversion segment 24 provide a twenty degree angle 74, 76 of retroversion. It is within the scope of the disclosure for the widths 78 of the slots 70, 72 to be greater than the widths 62 of the tabs 60, within limits, to provide the surgeon room to adjust the retroversion angle 74, 76, within limits, to more closely match the retroversion of the humeral bone being replaced. In one embodiment, the limits of adjustment of retroversion angle 74, 76 are between fifteen and thirty degrees. In another embodiment, the limits of the adjustment of the retroversion angle 74, 76 are set to mimic ranges of the retroversion angle found in normal healthy human beings.

In a second embodiment of the proximal component 222 and a second embodiment of the retroversion segment 224, the proximal component 222 is provided with an indicator mark 260 on its distal end 54 and the retroversion component 224 is provided with a plurality of alignment marks 276, 278 on its proximal end 83 to permit the surgeon infinite range and precision in varying the retroversion angle 76, 78 of the humeral prosthesis 200, 300 being formed.

Figure 4:
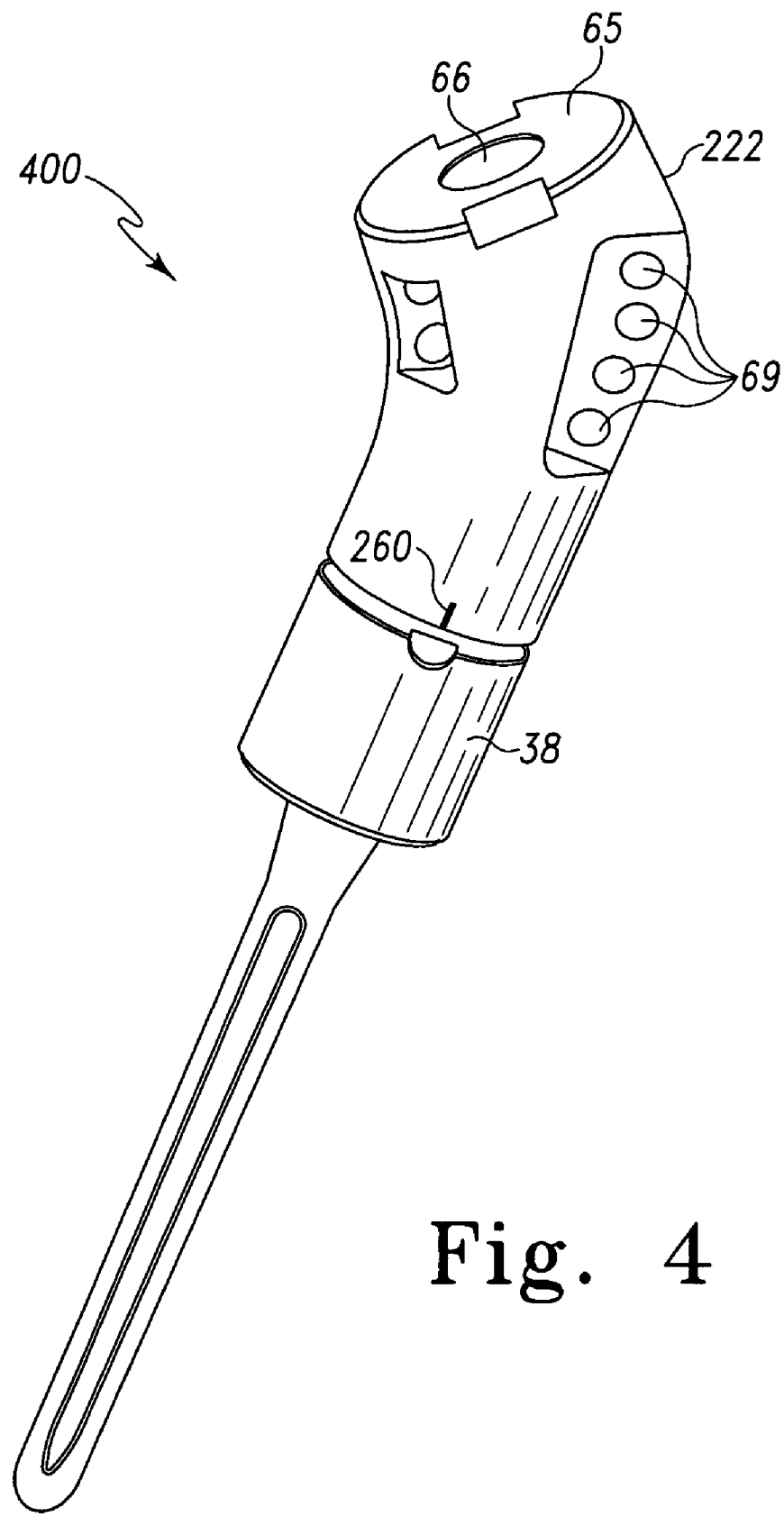
FIG. 4 is a perspective view of a modular long bone prosthesis (with the head removed for clarity) configured for proximal bone replacement having a second embodiment of a proximal component mated to the stem component of FIG. 1.

As shown for example, in FIG. 4, a proximal humeral prosthesis 400 is formed by mating a second embodiment of the proximal component 222, a selected stem component 38 and the head 42 (not shown for clarity). While shown as using stem component 38, the selected stem component could just as well be stem component 40. It is within the scope of the disclosure for one or more spacer segments 28, 30, 32, 34, alone or in combination, to be interposed between the proximal component 222 and the selected stem component 38 to form a proximal humeral prosthesis having an overall length appropriate for the length of the humerus being replaced and the degree of resection necessary for replacement. Thus, additional spacer segments 28, 30, 32, 34 are provided during the surgery for the surgeon to select to adjust the length of the proximal prosthesis 400. This feature is particularly useful when an unanticipated bone deficiency is discovered during surgery requiring greater resection than anticipated.

As shown, for example, in FIG. 5, a distal humeral prosthesis 500 is formed by mating a distal component 26 to a selected stem component 38. While shown as using stem component 38, the selected stem component could just as well be stem component 40. In the illustrated embodiment, the tabs 142 on the proximal end 139 of the distal component 26 are received in slots 112 formed in the body 100 of the stem component 38 to prevent rotation of the distal component 26 relative to the stem component 38. It is within the scope of the disclosure for one or more spacer segments 28, 30, 32, 34, alone or in combination, to be interposed between the distal component 26 and the selected stem component 38 to form a distal humeral prosthesis having an overall length appropriate for the length of the humerus being replaced and the degree of resection necessary for replacement.

As shown for example, in FIG. 6, an intercalary humeral prosthesis 600 is formed by mating the intercalary segment 28 to two stem components 38, 40. In the illustrated embodiment, the tabs 188, 190 on the opposite end walls 182, 184 of the intercalary component 36 are received in slots 112 formed in the body 100 of the stem components 38, 40 to prevent rotation of the intercalary segment 36 relative to the stem components 38, 40. It is within the scope of the disclosure for one or more spacer segments 28, 30, 32, 34, alone or in combination, to be interposed between the intercalary component 36 and one or both of the stem components 38, 40 to form an intercalary humeral prosthesis having an overall length appropriate for the length of the humerus being replaced and the degree of resection necessary for replacement. The intercalary segment 36 accepts stem components 38, 40 on either end to replace a section of bone between the shoulder and elbow. This intercalary prosthesis 600 is typically used during tumor and trauma procedures.

The manner of operation of the long bone prosthesis system 20 can be better understood by understanding the configuration and interaction of the various components 22, 24, 26, 28, 30, 32, 34, 36, 38, 40, 42 of the system 20. These components 22, 24, 26, 28, 30, 32, 34, 36, 38, 40, 42 are designed and configured to facilitate the above described assembly configurations 200, 300, 400, 500, 600. As previously mentioned, the prosthesis system 20 includes the proximal component 22, the retroversion segment 24, the distal component 26, the first, second, third and fourth spacer segments 28, 30, 32, 34, the intercalary segment 36, the first and second stem components 38, 40 and the head 42. The head 42 has already been described in sufficient detail and will not be described again. Additionally, since the head 42 is of the type commonly available, it is within the scope of the disclosure for kit 20 to not include head 42.

As previously mentioned, the illustrated stem components 38, 40 are virtually identical. Each stem component 38, 40 includes a generally cylindrical body 100, a Morse taper male stem 102, an intramedullary stem 104 and a longitudinal axis 106. The Morse taper male stem 102 extends from one end wall 108 of the cylindrical body 100 and the intramedullary stem 104 extends from the other end wall 110, as shown for example, in FIG. 1. The cylindrical body 100 and the Morse taper male stem 102 are formed concentrically about the longitudinal axis 106 and the intramedullary stem 104 is formed symmetrically about the longitudinal axis 106. The Morse taper male stem 102 is sized and configured to be received in a similarly sized Morse taper female socket present on other components 22, 26, 28, 30, 32, 34, 36 of the system 20. Similarly sized female sockets are found on the proximal component 22, the distal component 26, each spacer segment 28, 30, 32, 34 and the intercalary segment 36. Thus, each stem component 38, 40 is configured to mount to the proximal component 22, the distal component 26, each spacer segment 28, 30, 32, 34 and the intercalary segment 36 as need be to form an appropriately sized and configured proximal, distal or intercalary prosthesis 400, 500, 600.

While only a single slot 112 is shown in FIGS. 1, 4, 5, 7 on each stem component 38, 40, a set of slots 112 is formed in the end wall 108 and the side wall 101 of the stem component 38, 40 adjacent the Morse taper male stem 102. Illustratively two slots 112 are formed in each set of slots and the slots 112 in each set of slots are diametrically opposed on the cylindrical body 100. Illustratively, the slots 112 have a width 114 substantially equal to or slightly greater than the diametrically opposed tabs formed adjacent the Morse taper female bores on other components 22, 26, 28, 30, 32, 34, 36 of the long bone prosthesis system 20. The arrangement and widths of the illustrated slots and tabs ensure proper alignment of the various components when mated to form a prosthesis.

Each intramedullary stem 104 is configured and sized to be received in the intramedullary canal of the humerus. As previously mentioned, it is within the scope of the disclosure for other stem components to be provided with the modular prosthesis system 20 with such stem components being virtually identical to the illustrated stem components 38, 40 except for the size and length of the intramedullary stem 104. The illustrated intramedullary stem 104 is, for example, what is commonly called an eight millimeter stem. It is within the scope of the disclosure for the modular long bone prosthesis system 20 to be provided with stem components having intramedullary stems of other sizes including but not limited to six and ten millimeter stems.

As shown, for example, in FIGS. 1-3 and 7-8, the proximal component 22 includes a shaft portion 48 formed about a shaft longitudinal axis 49, a neck portion 50 formed about a neck longitudinal axis 51, a proximal end 52 and a distal end 54. Shaft portion 48 includes a generally cylindrical body 56 formed concentrically about the shaft longitudinal axis 49. The cylindrical body 56 includes a distal end wall 57 and a cylindrical side wall 58. A tapered bore 59 is formed in the body 56 of the shaft portion 48 extending inwardly from the distal end wall 57 and formed concentrically about the longitudinal axis 49. The tapered bore 59, illustratively is formed to function as a Morse taper female socket and is thus configured to mate in a locking fashion with a similarly sized Morse taper male stem. In the illustrated prosthesis system 20, each stem component 38, 40, each spacer segment 28, 30, 32, 34, and the retroversion segment 24 are formed to include a similarly sized Morse taper male stem and thus could be mounted directly to the distal end 54 of the proximal component 22.

Neck portion 50 of the proximal component 22 includes a side wall 64 that smoothly curves away from the cylindrical wall 58 of the shaft portion 48 until the side wall 64 is substantially cylindrical and centered about the neck longitudinal axis 51 at a point adjacent to the proximal end 52 of the proximal component 22. The neck longitudinal axis 51 forms an inclination angle 63 with the shaft longitudinal axis 49. In the illustrated embodiment this inclination angle 63 is forty-five degrees which is the average inclination angle found between the head and shaft of a human humerus.

The neck portion 50 includes a proximal end wall 65 through which a tapered bore 66 extends into the neck portion 50. The end wall 65 and the tapered bore 66 are formed concentrically about the longitudinal axis 51 and configured to mate with the stem 46 of the head 42 or another head of a shoulder prosthesis.

Figure 8:
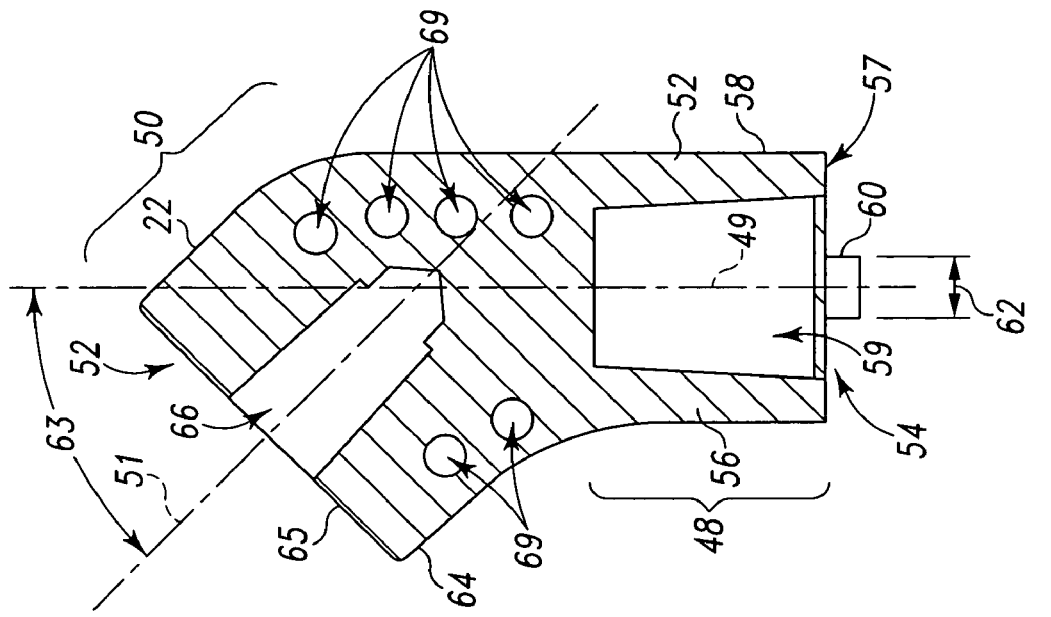
FIG. 8 is a sectional view of the proximal component taken along line 8-8 of FIG. 7.

As shown, for example, in FIGS. 2, 3 and 8, the illustrated proximal component 22 is configured to be joined to a head 42 with a reverse Morse taper lock. The stem 46 of the Morse taper lock is on the head 42. Other heads provided with current shoulder joint prosthesis systems include stems configured to be received in the tapered bore socket 66 of the proximal component 22. Thus, various head configurations and sizes can be used with the proximal component 22 to form total bone prosthesis 200, 300 or proximal prosthesis 400 to fit all body configurations. The head 42 will engage the natural glenoid if there is little or no glenoid erosion and a hemiarthroplasty may be performed. Otherwise, the head 42 will engage a glenoid prosthesis, such as that disclosed, for example, in U.S. Pat. No. 5,032,132.

As mentioned above in describing the assembly of the total bone prosthesis 200, 300, the distal end 54 of the proximal component 22 is formed to include a set of tabs 60 extending from the distal end wall 57 adjacent the Morse taper female socket 59. As shown, in FIGS. 7 and 8, the set of tabs includes two tabs 60 diametrically opposed on the shaft portion 48 of the proximal component 22. The tabs 60 are formed centered about a diametrical line 68 extending perpendicular to the plane in which the inclination angle 63 is formed. In the illustrations, the plane in which the angle of inclination 63 is formed is the plane of the paper with regard to FIG. 8 and perpendicular into the paper with regard to FIG. 7, thus the diametrical line 68 intersecting the centers of the two tabs 60 (and longitudinal axis 49) is parallel to the paper in FIG. 7 and into the paper in FIG. 8. This arrangement of the tabs 60 in the proximal component 22 and the arrangement of similar tabs in the distal component 26, and spacer segments 28, 30, 32, 34 and the arrangement of slots in the retroversion segment 24 and the spacer segments 28, 30, 32, 34 helps to maintain the components in specific orientations whereby the retroversion angles 76, 78 can be established in total bone prosthesis 200, 300. In the illustrated embodiment of the modular prosthesis system 20, the proximal component 22, distal component 26 and each spacer segment 28, 30, 32, 34 is formed to include a set of diametrically opposed tabs adjacent to a Morse taper female socket.

The proximal component 22 is formed to include suture and tape retention holes 69 facilitating attachment of various tendons, such as the subscapularis tendon to the humeral prosthesis 200, 300, 400 incorporating the proximal component 22. For instance in preparation for the humeral prosthesis, the subscapularis tendon is typically released from the humerus. After replacement of all or a proximal portion of the humerus with a prosthesis 200, 300, 400, the subscapularis tendon must be attached to the prosthesis. Typically several lengths of 1 mm non-absorbable tape are sutured to the subscapularis tendon to implement this repair. The proximal component 22 is provided with tape and suture receiving holes 69 for attachment of the subscapularis tendon and other tendons or tissue to the proximal component 22.

A second embodiment of the proximal component 222 provides many of the same advantages as the first embodiment 22 described above. As shown, for example, in FIGS. 1-4, 7, 8 and 14, the second embodiment of the proximal component 222 shares many features in common with the first embodiment of the proximal component 22. Thus, similar reference numerals (typically in a series 200 higher than used in describing the first embodiment) will be used in describing the second embodiment of the proximal component 222 as were used in describing the first embodiment of the proximal component 22. Where components are identical, the same reference numerals will be used in describing the second embodiment of the proximal component 222 as were used in describing the first embodiment of the proximal component 22. Generally speaking, however, only set of tabs 60 and the set of indicator marks 260 differ between the embodiments 22, 222.

Figure 15:
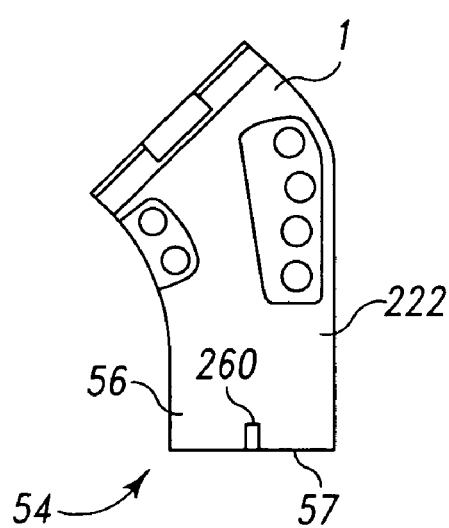
FIG. 15 is a side elevation view of a second embodiment of a proximal component of the modular prosthesis.

The second embodiment of the proximal component 222 is shown, for example, in FIGS. 4 and 15. The second embodiment of proximal prosthesis 222 is virtually identical to the first embodiment of proximal component 22. Thus, only the differences between the second embodiment of the proximal component 222 and the first embodiment of the proximal component 22 will be described with regard to the second embodiment. Instead of having a set of tabs 60 extending from the distal end wall 57 like the first embodiment of the proximal component 22, a set of indicator marks 260 are positioned on the cylindrical body 56 adjacent the distal end wall 57 in the second embodiment of the proximal component 222. Thus, proximal component 222 can be mounted on any component 24, 28, 30, 32, 34, 36, 38, 40 on which the proximal component 22 can be mounted to form total humeral prosthesis similar to 200 and 300 and a proximal humeral prosthesis 400. Since the tabs 60 are not present on the proximal component 222, the proximal component 222 is not limited in its orientation with respect to the component to which is mounted. Thus, a surgeon is free to set the retroversion angle 76, 78 at any value desired using the proximal component 222. When mated to another component, the Morse taper lock is relied upon to prohibit rotation of the proximal component 222 with respect to the component of the system 20 to which it is mounted.

Since both the first and second embodiments of the proximal component 22, 222 are intended for use in prosthetic devices, external surfaces 58, 64 of both of the proximal components 22, 222 are porous coated except for the area adjacent the Morse taper female socket 59 and the area adjacent to the suture holes 69. The porous coating aids in soft tissue attachment.

As shown, for example, in FIGS. 1, 2, 3 and 9-11, the retroversion segment 24 includes a cylindrical body 80, a proximal Morse taper male stem 82 and a distal Morse taper male stem 84 all formed concentrically about a longitudinal axis 86. Each Morse taper male stem 82, 84 is sized and configured to be received in similarly sized Morse taper female sockets present on other components 22, 26, 28, 30, 32, 34, 36 of the system 20. Similarly sized female sockets are found on the proximal component 22, the distal component 26, and each spacer segment 28, 30, 32, 34. Thus, retroversion segment 24 is configured to mount to the proximal component 22, the distal component 26, and each spacer segment 28, 30, 32, 34 as need be to form an appropriately sized and configured total bone prosthesis 200, 300.

As shown for example, in FIGS. 1 and 10, a set of slots 88 is formed in the distal end wall 90 and the side wall 92 of the retroversion segment 24 adjacent the distal Morse taper male stem 84. Illustratively two slots 88 are formed in each set of slots 88 and the slots 88 in each set of slots are diametrically opposed on the cylindrical body 80. Illustratively, the slots 88 have a width 91 substantially equal to or slightly greater than the width of the diametrically opposed tabs formed adjacent the Morse taper female bores on other components 22, 26, 28, 30, 32, 34 of the long bone prosthesis system 20.

As shown, for example, in FIGS. 1 and 9, a first set of slots 70 and a second set of slots 72 are formed in the proximal end wall 94 and the side wall 92 of the retroversion segment 24 adjacent the proximal Morse taper male stem 82. Illustratively two slots 70, 72 are formed in each set of slots and the slots 70, 72 in each set of slots 70, 72 are diametrically opposed on the cylindrical body 80. Illustratively, the slots 70, 72 have a width 78 substantially equal to or slightly greater than the diametrically opposed tabs formed adjacent the Morse taper female sockets on other components 22, 26, 28, 30, 32, 34 of the long bone prosthesis system 20.

Illustratively, the diametrical line 71 extending through the centers of the first set of slots 70 (and the longitudinal axis 86) forms a 20 degree angle 89 with a line parallel to the diametrical line 87 extending through the set of slots 88 on the distal end wall 90 of the retroversion segment 24. Similarly, the diametrical line 72 extending through the centers of the second set of slots 72 (and the longitudinal axis) forms a 20 degree angle 93 with a line parallel to the diametrical line 87 extending through the set of slots 88 on the distal end wall 90 of the retroversion segment 24. As will be explained further below, the arrangement and widths of the illustrated slots and tabs ensure proper alignment of the various components when mated to form a prosthesis.

A second embodiment of the retroversion segment 224 provides many of the same advantages as the first embodiment 24 described above. As shown, for example, in FIG. 16, the second embodiment of the retroversion segment 224 shares many features in common with the first embodiment of the retroversion segment 24. Thus, similar reference numerals (typically in a series 200 higher than used in describing the first embodiment) will be used in describing the second embodiment of the retroversion segment 224 as were used in describing the first embodiment of the retroversion segment 24. Where components are identical, the same reference numerals will be used in describing the second embodiment of the retroversion segment 224 as were used in describing the first embodiment of the retroversion segment 24. Generally speaking, however, only the fact that the set of slots 70, 72 is configured to include a set of alignment indicia or marks 270, 272 creates a difference between the embodiments of the retroversion segments 24, 224.

Figure 16:
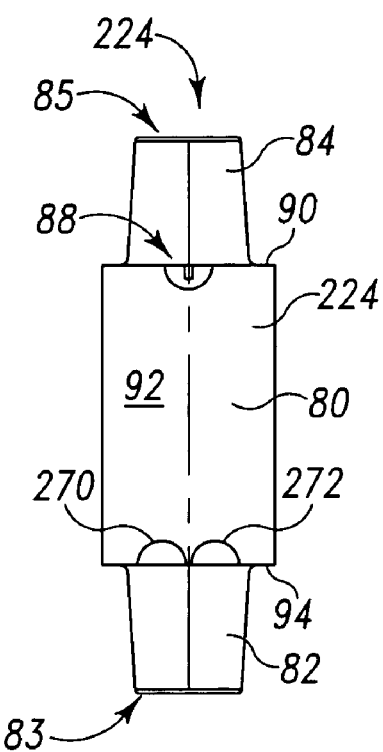
FIG. 16 is a side elevation view of a second embodiment of the retroversion component of the modular prosthesis.

The second embodiment of the retroversion segment 224 is shown for example in FIG. 16. The second embodiment of the retroversion segment 224 is virtually identical to the first embodiment of the retroversion segment 24. Thus, only the differences between the second embodiment of the retroversion segment 224 and the first embodiment of the retroversion segment 24 will be described with regard to the second embodiment. The two sets of slots 70, 72 formed in the proximal end wall 94 and the side wall 92 of the cylindrical body 80 are formed to include sets of alignment marks 270, 272 respectively. Thus, the retroversion segment 224 can be mounted on any component 22, 26, 28, 30, 32, 34, on which the retroversion segment 24 can be mounted to form total humeral prosthesis similar to 200 and 300 and a proximal humeral prosthesis 400.

Since the tabs 60 are not present the proximal component 222, the proximal component 222 is not limited in its orientation with respect to the retroversion segment 224 when mounted thereto. Thus, when using the proximal component 222 and the retroversion segment 224, a surgeon is free to set the retroversion angle 76, 78 at any value desired using the proximal component 222. If the angle desired is within the angles indicated by indicator marks 270, 272 on the retroversion segment 224, the surgeon can set the retroversion angle precisely by aligning the indicator mark 260 on the proximal component 222 with the appropriate alignment mark 270, 272 on the retroversion segment 224.

Either of the retroversion segments 24, 224 may be used to form a total humeral prosthesis 200, 300. Both retroversion segments 24, 224 have Morse taper male stems 82, 84 on the proximal and the distal ends 83, 85, respectively. In theory, a proximal humeral component 22, 222 is mounted on the proximal end 83 of the selected retroversion segment 24, 224 and the distal humeral component 26 is mounted on the distal end 85. However, this would be highly unlikely as the assembly of just these three components would not be of sufficient length to restore the arm back to its length prior to the surgery. To obtain the correct length, additional spacer segments 28, 30, 32, 34 are included in the total prosthesis 200, 300. The two sets of slots 70, 72 on the proximal end 83 of the retroversion segments 24, 224 serve two purposes. First, they provide the surgeon a reference for 20 degree retroversion of the humeral head relative to the axis of rotation of the distal humeral component (elbow). Second they permit the components 22, 24, 26, 28, 30, 32, 34 to be assembled to form either a right total bone prosthesis 200 or a left total bone prosthesis 300.

As shown, for example, in FIGS. 1, 2, 3, 5 and 14, the distal component 26 includes a joint portion 116 formed symmetrically about a longitudinal axis 117 and a shaft portion 118 formed concentrically about a longitudinal axis 119. The joint portion 116 of distal component 26 includes two parallel arms 120, 122 and an attachment area 121 extending at an inclination angle 123 relative to the longitudinal axis 119 of the shaft portion 118. The attachment area 121 is formed to include two flanges 127 through which suture holes 129 extend as shown in FIG. 1. The parallel arms 120, 122 are formed to include pivot pin mounting holes 124, 125 adjacent the distal ends 16, 128 of the arms 120, 122, respectively. The pivot pin mounting holes 124, 125 are formed concentrically about a rotation axis 130 perpendicular to the longitudinal axis 117 of the joint portion 116. The joint portion 116 is configured to mate with components of the Acclaim™ Total Elbow System available from DePuy Orthopaedics, Inc, Warsaw, Ind., a Johnson & Johnson company. The joint portion 116 is also configured to mate with portions of the elbow joint prosthesis disclosed in Weiss et al., U.S. Pat. No. 6,290,725, the disclosure of which is incorporated herein by this reference.

The shaft portion 118 includes a cylindrical body 132 and a proximal Morse taper female socket 134 both formed concentrically about the longitudinal axis 119. The cylindrical body 132 of the distal component 26 includes a distal end wall 128, a proximal end wall 138 and a cylindrical side wall 140. The tapered bore 134 is formed in the body 132 of the distal component 26 extending inwardly from the proximal end wall 138 and formed concentrically about the longitudinal axis 119. The tapered bore 134, illustratively, is formed to function as a Morse taper female socket and is thus configured to mate in a locking fashion with a similarly sized Morse taper male stem. In the illustrated prosthesis system 20, each stem component 38, 40, the retroversion segment 24 and each spacer segment 28, 30, 32, 34 are formed to include a similarly sized Morse taper male stem and thus could be mounted directly to the proximal end 139 of the distal component 26.

Figure 14:
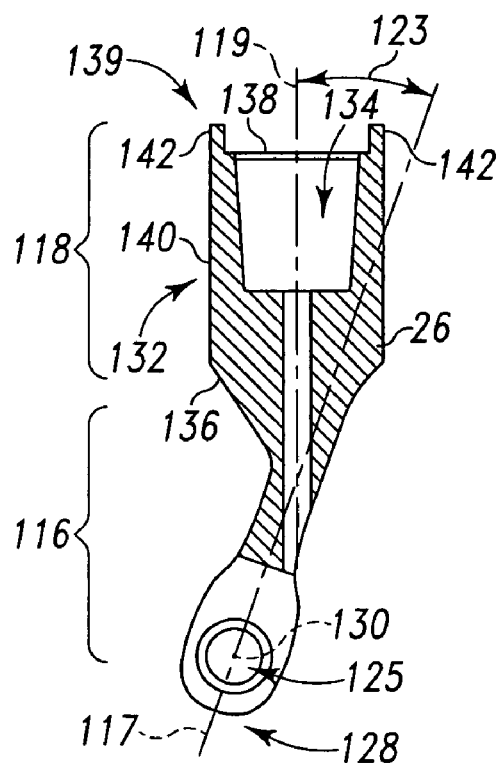
FIG. 14 is a sectional view of the distal component taken along line 14-14 of FIG. 1.

As shown for example, in FIGS. 1 and 14, a set of tabs 142 is formed extending from the proximal end wall 138 of the distal component 26 adjacent the proximal Morse taper female socket 134. Illustratively two tabs 142 are formed in each set of tabs and the tabs 142 in each set of tabs are diametrically opposed on the cylindrical body 140. Illustratively, the tabs 142 have a width 144 substantially equal to or slightly less than the width of the diametrically opposed slots formed adjacent the Morse taper male stems on the spacer segments 28, 30, 32, 34, the retroversion segment 24 and stem components 38, 40 of the long bone prosthesis system 20. As shown, for example, in FIG. 14, the tabs 142 are formed centered in a plane perpendicular to the rotation axis 130 of the forearm to which the distal component 26 is to be coupled.

As shown, for example, in FIGS. 1, 2, 3 and 12, the spacer segment 28 includes a cylindrical body 146, a distal Morse taper male stem 148 and a proximal Morse taper female socket 150 all formed concentrically about a longitudinal axis 152.

Except for the lengths of the respective cylindrical bodies 146, each spacer segment 28, 30, 32, 34 is identical. In the illustrated embodiment, the cylindrical body 146 of the spacer segment 28 has a length 154. Illustratively the length 154 is twenty millimeters. The cylindrical body 146 of the spacer segment 30 has a length 156. Illustratively the length 156 is twenty-five millimeters. The cylindrical body 146 of the illustrated spacer segment 32 has a length 158. Illustratively the length 158 is thirty millimeters. The cylindrical body 146 of the illustrated spacer segment 34 has a length 160. Illustratively the length 160 is thirty-five millimeters.

Thus, in the illustrated embodiment of modular prosthesis system 20, spacer segments 28, 30, 32, 34 are provided to facilitate incrementally increasing, once a spacer segment is used, the length of the prosthesis 200, 300, 400, 500, 600 being formed In the illustrated modular prosthesis system 20, the length of the prosthesis 200, 300, 400, 500, 600 being formed may be increased in five millimeter increments. It is within the scope of the disclosure for spacer segments 28, 30, 32, 34 to be provided having differing lengths and facilitating adjustment of the length of prosthesis in other incremental amounts. Similarly, it is within the scope of the disclosure to provide a spacer segment with a continuously adjustable length configured to mate with the other components 22, 24, 26, 38, 40 of the system.

Since the illustrated spacer segments 28, 30, 32, 34 only differ in the length 154, 156, 158, 160 of the body 146, spacer segment 28 will be described with the understanding that that description is applicable to the other spacer segments 30, 32, 34. The cylindrical body 146 of the spacer segment 28 includes a distal end wall 162, a proximal end wall 164 and a cylindrical side wall 166. The tapered bore 150 is formed in the body 146 of the spacer segment 28 extending inwardly from the proximal end wall 164 and formed concentrically about the longitudinal axis 152. The tapered bore 150, illustratively is formed to function as a Morse taper female socket and is thus configured to mate in a locking fashion with a similarly sized Morse taper male stem. In the illustrated prosthesis system 20, each stem component 38, 40, each spacer segment 28, 30, 32, 34, and the retroversion segment 24 are formed to include a similarly sized Morse taper male stem and thus could be mounted directly to the proximal end 165 of the spacer segment 28.

The distal Morse taper male stem 148 extends outwardly from the distal-end wall 162 of the spacer segment 28. The distal Morse taper male stem 148 is sized and configured to be received in a similarly sized Morse taper female socket present on other components 22, 26, 28, 30, 32, 34, 36 of the system 20. Similarly sized Morse taper female sockets are found on the proximal component 22, the distal component 26, and each spacer segment 30, 32, 34. Thus, spacer segment 28 is configured to mount to the proximal component 22, the distal component 26, and each spacer segment 28, 30, 32, 34 as need be to form an appropriately sized and configured total bone prosthesis 200, 300, 400, 500, 600.

As shown for example, in FIGS. 1 and 12, a set of slots 168 is formed in the distal end wall 162 and the side wall 166 of the spacer segment 28 adjacent the distal Morse taper male stem 148. Illustratively two slots 168 are formed in each set of slots and the slots 168 in each set of slots are diametrically opposed on the cylindrical body 146. Illustratively, the slots 168 have a width 169 substantially equal to or slightly greater than the width of the diametrically opposed tabs formed adjacent the Morse taper female sockets on other components 22, 26, 28, 30, 32, 34 of the long bone prosthesis system 20.

Similarly, the proximal end 165 of the spacer segment 28 is formed to include a set of tabs 170 extending from the proximal end wall 164 adjacent the proximal Morse taper female socket 150. As shown, in FIGS. 1 and 12, the set of tabs 170 includes two tabs diametrically opposed on spacer segment 28. As shown, for example, in FIG. 12, the tabs 170 are formed centered in the same plane as the slots 168 and the longitudinal axis 152. The tabs 170 have a width approximately equal to or slightly smaller than the width of the slots formed adjacent the Morse taper male stems on other components 24, 30, 32, 34, 38, 40 of the modular prosthesis system 20.

A second embodiment of the spacer segment 228 provides many of the same advantages as the first embodiment 28 described above. As shown, for example, in FIG. 17, the second embodiment of the spacer segment 228 shares many features in common with the first embodiment of the spacer segment 28. Thus, similar reference numerals (typically in a series 200 higher than used in describing the first embodiment) will be used in describing the second embodiment of the spacer segment 228 as were used in describing the first embodiment of the spacer segment 28. Where components are identical, the same reference numerals will be used in describing the second embodiment of the spacer segment 228 as were used in describing the first embodiment of the spacer segment 28.

Figure 17:
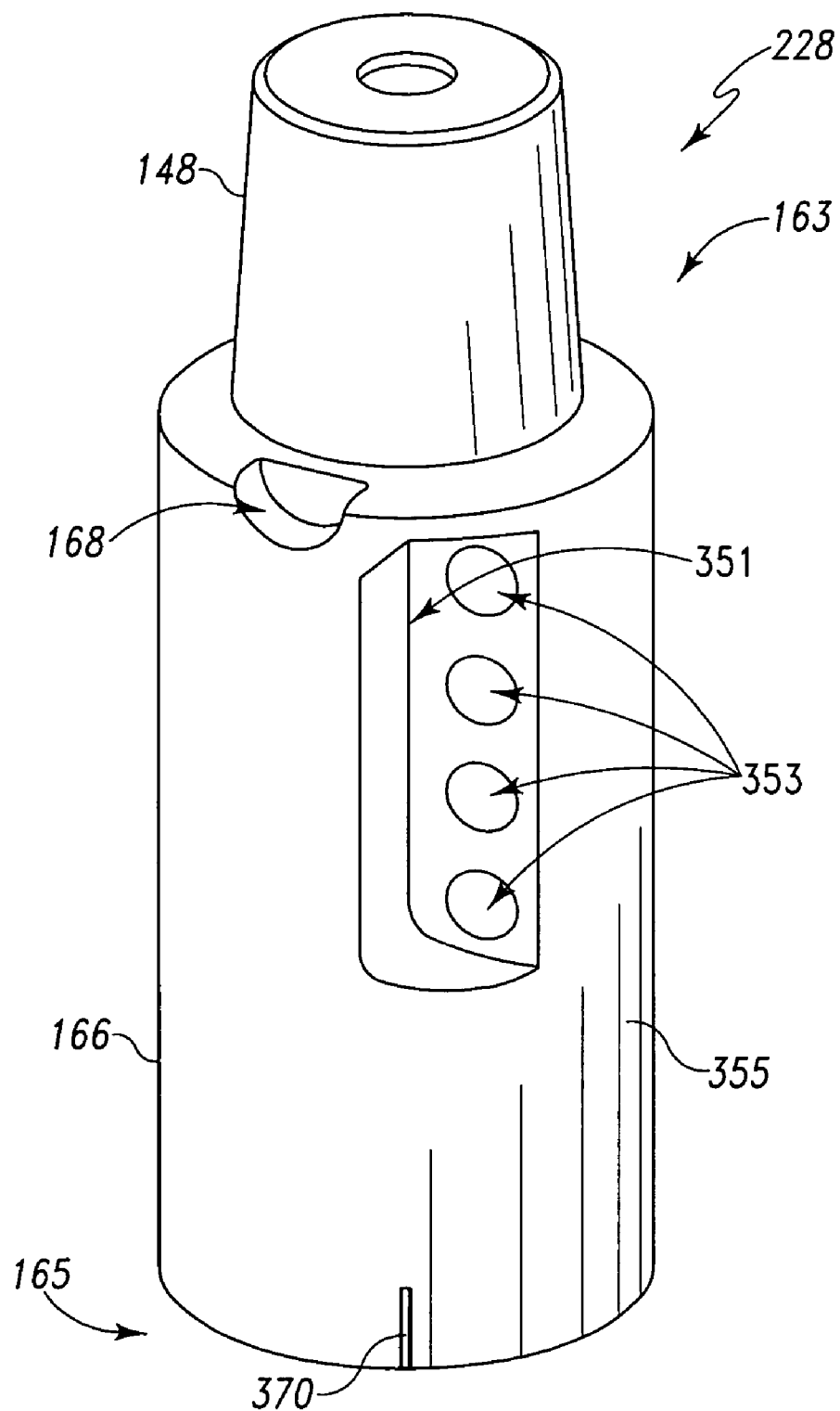
FIG. 17 is a perspective view of a second embodiment of a spacer segment.

The second embodiment of the spacer segment 228 is shown for example in FIG. 17. The second embodiment of the spacer segment 228 is virtually identical to the first embodiment of the spacer segment 28. Thus, only the differences between the second embodiment of the spacer segment 228 and the first embodiment of the spacer segment 28 will be described with regard to the second embodiment. The second embodiment of the spacer segment 28 does not include a set of tabs 170 extending from the proximal end wall 164. Rather, the side wall 166 of the cylindrical body 146 is formed to include a set of diametrically opposed indicator marks 330. Thus, the spacer segment 228 can be mounted on any component 22, 26, 28, 30, 32, 34 36, 38, 40 on which the spacer segment 28 can be mounted to form humeral prosthesis similar to 200, 300, 400, 500, 600. While not illustrated, it is within the scope of the disclosure for the set of slots 168 on the distal end 163 to be either formed to include a set of alignment marks or indicia therein or be eliminated and replaced with a set of alignment marks or indicia.

The cylindrical side wall 166 of the spacer segment 228 is formed to include indentations 351 forming a rib 355 through which suture holes 353 are formed. During total humeral replacement, proximal humeral replacement, intercalary replacement, and sometimes during distal humeral replacement, the portion of the humerus to which the ligament connecting the distal end of the deltoid is attached must be removed. The suture holes 353 provide a site for attaching the deltoid ligament to the prosthesis 200, 300, 400, 500, 600 when assembled using the spacer segment 228.

The illustrated spacer segments 28, 228, 30, 32, 34 are porous coated except for the Morse taper male stem 148 and the Morse taper female socket 150 and, on spacer segment 228, the area adjacent to the suture holes 353. Spacer segment 228 would typically be used in proximal humeral and total humeral replacements. Spacer segment 228 can be assembled directly to the porous coated proximal humeral component 22.

Alternatively, the retroversion segment 24, alone or in combination with one or more spacer segments 28, 30, 32, 34, could be assembled in between the spacer segment 228 and the proximal component 22. Thus, the surgeon has the ability to adjust the location of additional porous coating area, i.e. the spacer segment 228 may be positioned distally from the proximal component 22 as needed to re-attach the deltoid ligament as anatomically correctly as possible.

As shown, for example, in FIGS. 1, 6 and 13, the intercalary segment 36 includes a cylindrical body 174, a distal Morse taper female socket 176 and a proximal Morse taper female socket 178 all formed concentrically about a longitudinal axis 180. The cylindrical body 174 of the intercalary segment 36 includes a distal end wall 182, a proximal end wall 184 and a cylindrical side wall 186. The proximal Morse taper female socket 178 is formed in the body 174 of the intercalary segment 36 extending inwardly from the proximal end wall 184 and formed concentrically about the longitudinal axis 180. Similarly, the distal Morse taper female socket 176 is formed in the body 174 of the intercalary segment 36 extending inwardly from the distal end wall 182 and formed concentrically about the longitudinal axis 180. Both the proximal Morse taper female socket 178 and the distal Morse taper female socket 176 are configured to mate in a locking fashion with a similarly sized Morse taper male stem. In the illustrated prosthesis system 20, each stem component 38, 40, and each spacer segment 28, 30, 32, 34 are formed to include a similarly sized Morse taper male stem and thus could be mounted directly to the proximal or distal ends of the intercalary segment 36.

As shown, for example, in FIGS. 1 and 13, a set of tabs 188 is formed extending from the distal end wall 182 of the intercalary segment 36 adjacent the distal Morse taper female socket 176. Illustratively two tabs 188 are formed in each set of tabs and the tabs 188 in each set of tabs are diametrically opposed on the cylindrical body 174. Similarly, a set of tabs 190 is formed extending from the proximal end wall 184 of the intercalary segment 36 adjacent the proximal Morse taper female socket 178. Illustratively two tabs 190 are formed in each set of tabs and the tabs 190 in each set of tabs are diametrically opposed on the cylindrical body 174. Illustratively, the tabs 188, 190 have a width 192 substantially equal to or slightly less than the diametrically opposed slots formed adjacent the Morse taper male stems on the spacer segments 28, 30, 32, 34 and stem components 38, 40 of the long bone prosthesis system 20. As shown, for example, in FIG. 13, the tabs 188 are formed centered in the same plane as the tabs 190 and the longitudinal axis 180.

Now that each of the components of the humeral prosthesis system 20 have been described in detail, certain aspects of the prosthesis formed from the kit 20 can be better understood. In particular, in describing the right total humeral prosthesis 200 and the left total humeral prosthesis 300, reference was made to setting the retroversion angle 74, 76. The retroversion angle 74, 76 being formed is meaningless without a point of reference. The retroversion angle is defined according to the axis of rotation 130 of the forearm (in particular the ulna) with respect to the head of the humerus. The axis of rotation 130 of the forearm is perpendicular to the longitudinal axis of the shaft of the humerus. The head and neck of the humerus are formed about an axis that is angled downwardly with respect to the longitudinal axis of the humerus (the inclination angle) and rearwardly with respect to the plane including the axis of rotation 130 of the forearm and a line parallel to the longitudinal axis of the humerus.

As previously stated, and as shown, for example, in FIGS. 2 and 3, a full bone prosthesis 200, 300 includes the head 42, the proximal component 22, the retroversion segment 24, a spacer segment 28 and the distal component 26. Each of these components, other than the head 42, includes a longitudinal axis that, when assembled, is co-linear with the longitudinal axis of the other components. Thus, the longitudinal axis 119 of the shaft portion 118 of the distal component 26, the longitudinal axis 152 of the spacer segment 28, the longitudinal axis 86 of the retroversion segment 24 and the longitudinal axis 49 of the shaft portion 48 of the proximal component 22 are co-linear when the components 22, 24, 26, 28 are assembled to form a full bone prosthesis 200, 300.

The distal component 26 includes the pivot axis 130 extending between its two arms 120, 122 which provides a base line from which the retroversion angle 74, 76 is measured. In the illustrated embodiment of the distal component 26, the tabs 142 are formed on the proximal end wall 138 of the distal component 26 for receipt in slots formed in the component mating with the distal component 26. These tabs 142 are diametrically opposed about the longitudinal axis 119 of the shaft portion 118 of the distal component 126. The axis of rotation 130 of the forearm is perpendicular to (but not intersecting) the diameter extending through the centers of the tabs 142.

As shown, for example, in FIGS. 1 and 12, each spacer segment 28, 30, 32, 34 is formed with diametrically opposed tabs 170 on its proximal end wall 164 and diametrically opposed slots 168 on its distal end wall 162 with the diameters intersecting the centers of the tabs 170 and slots 168 being parallel to each other and perpendicular to and intersecting the longitudinal axis 152 of the segment 28, 30, 32, 34. Thus, when the tabs 142 on the distal component are inserted in the slots 168 on the spacer segment 28, 30, 32, 34, the diameters intersecting the tabs 170 and the slots 168 on the spacer segment 28, 30, 32, 34 remain parallel to each other and become parallel to the diameter intersecting the tabs 142 on the distal component 26. Thus, since the diameter intersecting the tabs 142 on the distal component 26 is perpendicular to the axis of rotation 130 of the forearm, the diameter intersecting the tabs 170 on the spacer segment 28, 30, 32, 34 is perpendicular to the axis of rotation 130 of the forearm when the spacer segment 28, 30, 32, 34 is assembled to the distal component 26.

When the tabs 170 of the spacer segment 28, 30, 32, 34 are received in the slots 88 on the distal end of the retroversion segment 24, the diameter intersecting the tabs 170 is parallel with the diameter intersecting the slots 88. Thus, when the retroversion component 24, spacer segment 28, 30, 32, 34 and distal component are assembled, as shown, for example, in FIGS. 2, 3, the diameter 87 through the slots 88 on the distal end 85 of the retroversion component 24 is perpendicular to the axis of rotation 130 of the forearm.

As shown in FIGS. 1, 9, 10, 11, the diameter 71 intersecting the first set of slots 70 on the proximal end 83 of the retroversion segment 24 is rotated clockwise twenty degrees with respect to the diameter 87 intersecting the set of slots 88 on the distal end 85 of the retroversion segment 24 (as viewed looking along the longitudinal axis 86 from the proximal end 83 toward the distal end 85 as shown, for example, in FIG. 9). Since the diameter 87 through the slots 88 on the retroversion segment 24 is perpendicular to the axis of rotation 130 of the forearm when the retroversion component 24, spacer segment 28, 30, 32, 34 and distal component 26 are assembled, as shown, for example, in FIGS. 2, 3, then the diameter 71 extending through the first set of slots 70 is rotated twenty degrees from perpendicular with respect to the rotation axis 130 of the forearm when the components are so assembled.

Figure 7:
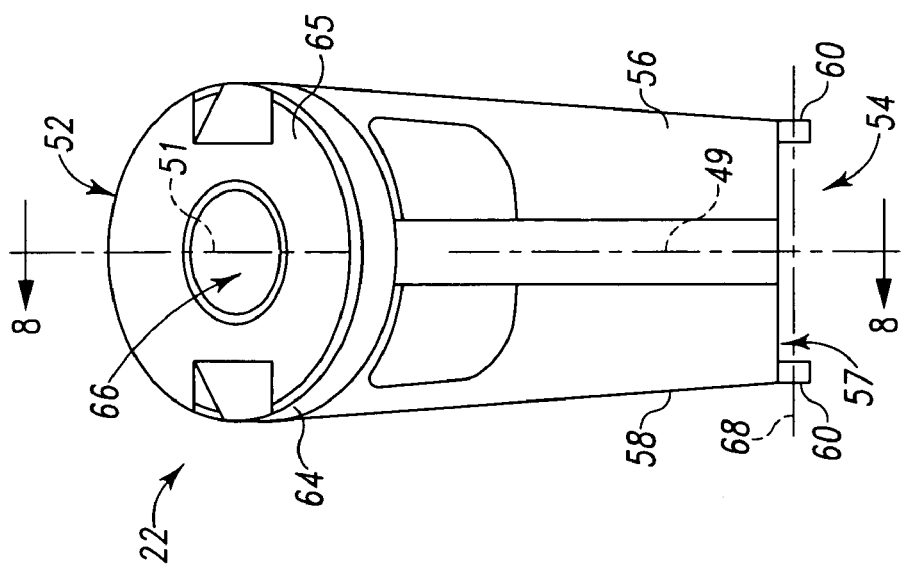
FIG. 7 is a front elevation view of the proximal component of FIG. 1.

As shown, for example, in FIGS. 1, 7, 8, proximal portion 22 is formed so that the tabs 60 extending from the distal end 54 are formed on a diameter 68 perpendicular to the plane in which the angle of inclination 63 (formed by the intersection of the longitudinal axis 51 of the neck component 50 with the longitudinal axis 49 of the shaft portion 48) is formed. Thus when the tabs 60 of the proximal portion 22 are received in the first set of slots 70 on the proximal end 83 of the retroversion segment 24, the plane in which the inclination angle is formed forms a twenty degree angle with the plane parallel to the longitudinal axis in which the rotation angle 130 is formed. When tabs 60 of the proximal component 22 are received in the first set of slots 70 of the retroversion component 24, the tabs 170 of the spacer segment 28, 30, 32, 34 are received in the slots 88 on the distal end 85 of the retroversion component 24, and the tabs 142 of the distal component 26 are received in the slots 168 of the spacer segment 28, 30, 32, 34, the plane in which the inclination angle 63 is formed is rotated twenty degrees with respect to the pivot axis 130 of the forearm. This twenty degree rotation creates the twenty degree retroversion angle 74 of the head 42 of the right long bone total prosthesis 200 with respect to the angle of rotation 130 of the forearm to be coupled thereto.

The diameter 73 intersecting the second set of slots 72 on the proximal end 83 of the retroversion segment 24 is rotated twenty degrees with respect to the diameter 87 intersecting the set of slots 88 on the distal end 85 of the retroversion segment 24 (as viewed looking along the longitudinal axis 86 from the proximal end 83 toward the distal end 85 as shown, for example, in FIG. 9). Since the diameter 87 through the slots 88 on the retroversion segment 24 is perpendicular to the axis of rotation 130 of the forearm when the retroversion component 24, spacer segment 28, 30, 32, 34 and distal component 26 are assembled, as shown, for example, in FIGS. 2, 3, then the diameter 73 extending through the second set of slots 72 is rotated twenty degrees from perpendicular with respect to the rotation axis 130 of the forearm when the components are so assembled.

Thus, when the tabs 60 of the proximal portion 22 are received in the second set of slots 72 on the proximal end 83 of the retroversion segment 24, the plane in which the inclination angle 63 is formed forms a twenty degree angle with the plane parallel to the longitudinal axis in which the rotation angle 130 is formed. When tabs 60 of the proximal component 22 are received in the second set of slots 72 of the retroversion component 24, the tabs 170 of the spacer segment 28, 30, 32, 34 are received in the slots 88 on the distal end 85 of the retroversion component 24, and the tabs 142 of the distal component 26 are received in the slots 168 of the spacer segment 28, 30, 32, 34, the plane in which the inclination angle 63 is formed is rotated twenty degrees with respect to the pivot axis 130 of the forearm. This twenty degree rotation creates the twenty degree retroversion angle 76 of the head 42 of the left long bone total prosthesis 300 with respect to the angle of rotation 130 of the forearm to be coupled thereto.

Thus, the tabs 60, 142, 170 on the proximal component 22, distal component 26 and spacer segment 28, 228, 30, 32, 34, respectively, act as indicators and the slots 70, 72, 88, 168, formed in the proximal end wall 94 and distal end wall 92 of the retroversion segment 24 and in the spacer segments 28, 30, 32, 34, respectively, act as alignment marks to ensure proper assembly of the components. When the widths of the tabs 60, 142, 170 are approximately equal to or slightly less than the widths of the slots 70, 72, 88, 168, insertion of the tabs 60, 142, 170 into the slots 70, 72, 88, 168 during assembly of the components 22, 24, 224, 26, 28, 30, 32, 34, 36 ensures precisely two possible configurations, assuming one and only one retrograde segment 24, 224 is used in the assembly, of the total bone prosthesis. One configuration is a right total bone prosthesis 200 with a twenty degree retroversion angle 74 and the other configuration is a left total bone prosthesis 300 with a twenty degree retroversion angle 76. When the slots 70, 72, 88, 168 are wider than the tabs 60, 142, 170, a right and left long bone prosthesis can be formed by the components 22, 24, 224, 26, 28, 30, 32, 34 with the retroversion angles 74, 76 adjustable within limits. When proximal component 224 and or the segment 228 wherein the tabs are eliminated are used to form a prosthesis, the retroversion angles 74, 76 are infinitely adjustable to form right or left total bone prosthesis.

Those skilled in the art will recognize that the terms distal and proximal are only relative terms as used with regard to the retroversion segment 22, the spacer segments 28, 30, 32, 34 and the intercalary segment 36 since any of these components could be oriented in the direction opposite to that shown in FIGS. 2, 3, and 6 to form the prosthesis 200, 300 or 600. Thus, when a total humeral prosthesis, similar to total humeral prosthesis 200, 300, is formed, the end of the retroversion section 24 including the two sets of slots 70, 72 could be mated with the distal component 62 or a spacer segment 28, 30, 32, 34 within the scope of the disclosure.

Although the invention has been described in detail with reference to a certain preferred embodiment, variations and modifications exist within the scope and spirit of the present invention as described and defined in the following claims.

What is claimed is:

1. A modular long bone prosthesis system for replacing all or a portion of a long bone having a head and neck at its proximal end and a pivot axis about which the bone with which the long bone articulates pivots at the distal end, the system comprising:

a proximal component configured to replace the neck of the long bone and to receive a component for replacing the head at a proximal end, a distal component configured at its distal end to include a pivot axis about which the bone with which the long bone articulates may pivot, a retroversion component, a spacer component, and a stem component and wherein:

the proximal component is configured on its distal end to mount to one of the retroversion component, the stem component and the spacer component;

the distal component is configured on its proximal end to mount to one of the retroversion component, the stem component and the spacer component;

the retroversion component is configured to mount at one end to one of the distal component and the spacer component and at the other end to one of the proximal component and the spacer component;

the spacer component is configured at one end to mount to one of the distal component and the proximal component and at the other end to mount to one of the retroversion component and the stem component;

the stem component is configured at one end to couple to one of the distal component, the proximal component and the spacer component and configured at the other end to be received in the intramedullary canal of the long bone; and wherein the proximal component, distal component and retroversion component when coupled form a total long bone prosthesis exhibiting a retroversion angle found in the long bone, the proximal and stem components when coupled form a proximal prosthesis, and the distal and stem components when coupled form a distal prosthesis;

wherein the proximal component, distal component and retroversion component when coupled in a first configuration form a right total long bone prosthesis and when coupled in a second configuration form a left total long bone prosthesis;

wherein the spacer segment when coupled between the proximal and distal components of the total long bone prosthesis forms a longer total long bone prosthesis;

further comprising a plurality of spacer components each having a differing length and configured at one end to mount to one of the distal component and the proximal component and at the other end to mount to one of the retroversion component and the stem component;

and further comprising a second stem component and an intercalary component configured at both ends to mount to one of a stem component and a spacer component and the intercalary component first stem component and second stem component when coupled form an intercalary prosthesis.

2. A modular long bone prosthesis system for replacing all or a portion of a long bone having a head and neck at its proximal end and a pivot axis about which the bone with which the long bone articulates pivots at the distal end, the system comprising;

a proximal component configured to replace the neck of the long bone and to receive a component for replacing the head at a proximal end, a distal component configured at its distal end to include a pivot axis about which the bone with which the long bone articulates may pivot, a retroversion component, a spacer component, and a stem component and wherein:

the proximal component is configured on its distal end to mount to one of the retroversion component, the stem component and the spacer component;

the distal component is configured on its proximal end to mount to one of the retroversion component, the stem component and the spacer component;

the retroversion component is configured to mount at one end to one of the distal component and the spacer component and at the other end to one of the proximal component and the spacer component;

the spacer component is configured at one end to mount to one of the distal component and the proximal component and at the other end to mount to one of the retroversion component and the stem component;

the stem component is configured at one end to couple to one of the distal component, the proximal component and the spacer component and configured at the other end to be received in the intramedullary canal of the long bone; and wherein the proximal component, distal component and retroversion component when coupled form a total long bone prosthesis exhibiting a retroversion angle found in the long bone, the proximal and stem components when coupled form a proximal prosthesis, and the distal and stem components when coupled form a distal prosthesis, wherein the spacer component is formed to include a suture attachment location for attachment of a ligament of a muscle to the prosthesis.

3. A modular humeral prosthesis system for replacing all or a proximal part of either a right or left human humerus having a head forming a retroversion angle with the pivot axis of the forearm, the system comprising:

a proximal component configured to replace the neck of the humerus and to receive a component for replacing the head of the humerus at a proximal end, a distal component configured at its distal end to include a pivot axis about which the forearm pivots, a retroversion component, a plurality of spacer components, and a stem component, wherein:

the proximal component is configured on its distal end to mount to one of the retroversion component, the stem component and one of the plurality of the spacer components;

the distal component is configured on its proximal end to mount to one of the retroversion component, the stem component and one of the plurality of the spacer components;

the retroversion component is configured to mount at one end to one of the distal component and one of the plurality of the spacer components and at the other end to one of the proximal component and one of the plurality of the spacer components;

each spacer component is configured at one end to mount to one of the distal component and the proximal component and at the other end to mount to one of the retroversion component and the stem component and one of the plurality of spacer components is longer than the other of the plurality of spacer components;

the stem component is configured at one end to couple to one of the distal component, the proximal component and the spacer component and configured at the other end to be received in the intramedullary canal of the long bone; and wherein the proximal component, distal component and retroversion component when coupled form a total humeral prosthesis exhibiting a retroversion angle found in the humerus, the proximal and stem components when coupled form a proximal humeral prosthesis, and the distal and stem components when coupled form a distal humeral prosthesis, wherein when the proximal component, distal component and retroversion component are mounted in a first orientation, a right total humeral prosthesis is formed, and wherein when the proximal component, distal component and retroversion component are mounted in a second orientation, a left total humeral prosthesis is formed, wherein one of the proximal component and the retroversion component is formed to include an indicator mark and the other of the proximal component and retroversion component is formed to include a first alignment mark and a second alignment mark and wherein when the indicator is aligned with the first alignment mark, the proximal component, distal component and retroversion component are mounted in the first orientation and when the indicator mark is aligned with the second alignment mark the proximal component, distal component and retroversion component are mounted in the second orientation, and wherein the indicator is a tab and the first alignment mark is a slot.

4. A modular long bone prosthesis, comprising:
a proximal component having a first coupler at a proximal end thereof and a second coupler at a distal end thereof;
a retroversion component having third coupler at a proximal end thereof and a fourth coupler at a distal end thereof, said third coupler being configured to mate with said second coupler of said proximal component so as to retain said retroversion component in fixed relation to said proximal component;
a head component having a fifth coupler configured to mate with the first coupler of said proximal component so as to retain said head component in fixed relation to said proximal component,
wherein said one of said proximal component and said retroversion component has a tab, and
wherein the other one of said proximal component and said retroversion component has a first slot and a second slot,
wherein said proximal component and said retroversion component are configurable between a right long bone mode and a left long bone mode,
wherein when in said right long bone mode (i) said second coupler of said proximal component is positioned in mating relationship with said third coupler of said retroversion component, (ii) said tab is positioned in said first slot, and (iii) no tab is positioned in said second slot, and
wherein when in said left long bone mode (i) said second coupler of said proximal component is positioned in mating relationship with said third coupler of said retroversion component, (ii) said tab is positioned in said second slot, and (iii) no tab is positioned in said first slot.

5. The modular long bone prosthesis of claim 4, further comprising:
an additional bone component having a sixth coupler configured to mate with said fifth coupler of said retroversion component so as to retain said retroversion component in fixed relation to said additional bone component.

6. The modular long bone prosthesis of claim 4, further comprising:
a spacer component having (i) aسسsixth coupler at a proximal end thereof, said sixth coupler being configured to mate with said fifth coupler of said retroversion component so as to retain said retroversion component in fixed relation to said spacer component, and (ii) a seventh coupler at a distal end thereof; and
a distal component having (i) an eighth coupler at a proximal end thereof, said eighth coupler being configured to mate with said seventh coupler of said spacer component, and (ii) a ninth coupler configured to attach to a joint prosthesis component.

7. The modular long bone prosthesis of claim 6, wherein:
said proximal component, said retroversion component, said head component, said spacer component, and said distal component collectively comprise a humeral prosthesis, and
said joint prosthesis component is an ulnar prosthesis component.

8. The modular long bone prosthesis of claim 4, wherein said first slot and said second slot are positioned adjacent to each other.

9. The modular long bone prosthesis of claim 4, wherein:
said retroversion component defines a central axis, and
when said retroversion component is viewed in a plan view in a direction defined by said central axis, (i) said first slot defines a first slot center point, (ii) said second slot defines a second slot center point, (iii) said first slot center point is offset from said second slot center point by θ° along an outside periphery of said retroversion component, and (iv) $10° \leq \theta \leq 90°$.

10. The modular long bone prosthesis of claim 9, wherein θ is about 40°.

11. A modular long bone prosthesis, comprising:
a proximal component having a first coupler;
a retroversion component having second coupler being configured to mate with said first coupler of said proximal component so as to retain said retroversion component in fixed relation to said proximal component;
wherein said one of said proximal component and said retroversion component has a tab, and
wherein the other one of said proximal component and said retroversion component has a first slot and a second slot,
wherein said proximal component and said retroversion component are configurable between a right long bone mode and a left long bone mode,
wherein when in said right long bone mode (i) said first coupler of said proximal component is positioned in mating relationship with said second coupler of said retroversion component, (ii) said tab is positioned in said first slot, and (iii) no tab is positioned in said second slot, and
wherein when in said left long bone mode (i) said first coupler of said proximal component is positioned in mating relationship with said second coupler of said retroversion component, (ii) said tab is positioned in said second slot, and (iii) no tab is positioned in said first slot.

12. The modular long bone prosthesis of claim 11, further comprising an additional bone, wherein:
said retroversion component has a third coupler positioned, and
said additional bone component has a fourth coupler configured to mate with said third coupler of said retroversion component so as to retain said retroversion component in fixed relation to said additional bone component.

13. The modular long bone prosthesis of claim 4, wherein said retroversion component has a third coupler, further comprising:
a spacer component having (i) a fourth coupler configured to mate with said third coupler of said retroversion component so as to retain said retroversion component in fixed relation to said spacer component, and (ii) a fifth coupler; and
a distal component having (i) a sixth coupler configured to mate with said fifth coupler of said spacer component, and (ii) a seventh coupler configured to attach to a joint prosthesis component.

14. The modular long bone prosthesis of claim 13, wherein:
said proximal component, said retroversion component, said spacer component, and said distal component collectively comprise a humeral prosthesis, and
said joint prosthesis component is an ulnar prosthesis component.

15. The modular long bone prosthesis of claim 11, wherein said first slot and said second slot are positioned adjacent to each other.

16. The modular long bone prosthesis of claim 11, wherein:
said retroversion component defines a central axis, and
when said retroversion component is viewed in a plan view in a direction defined by said central axis, (i) said first slot defines a first slot center point, (ii) said second slot defines a second slot center point, (iii) said first slot center point is offset from said second slot center point by θ° along an outside periphery of said retroversion component, and (iv) $10° \leq \theta \leq 90°$.

17. The modular long bone prosthesis of claim 16, wherein θ is about 40°.

* * * * *